US010022102B2

(12) United States Patent
Okada

(10) Patent No.: US 10,022,102 B2
(45) Date of Patent: Jul. 17, 2018

(54) RADIOGRAPHIC IMAGING APPARATUS, METHOD AND SYSTEM

(71) Applicant: FUJIFILM Corporation, Tokyo (JP)

(72) Inventor: Yoshihiro Okada, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 703 days.

(21) Appl. No.: 14/551,846

(22) Filed: Nov. 24, 2014

(65) Prior Publication Data

US 2015/0078528 A1  Mar. 19, 2015

Related U.S. Application Data

(63) Continuation of application No. PCT/JP2013/064474, filed on May 24, 2013.

(30) Foreign Application Priority Data

May 25, 2012  (JP) .................................. 2012-119607

(51) Int. Cl.
*G01T 1/02* (2006.01)
*G01T 1/15* (2006.01)
(Continued)

(52) U.S. Cl.
CPC .............. *A61B 6/542* (2013.01); *G01T 1/026* (2013.01); *G01T 1/15* (2013.01); *H05G 1/44* (2013.01);
(Continued)

(58) Field of Classification Search
CPC .... A61B 6/00; A61B 6/10; A61B 6/42; A61B 6/4233; A61B 6/54; A61B 6/542;
(Continued)

(56) References Cited

U.S. PATENT DOCUMENTS 5,894,129 A * 4/1999 Pool ....................... A61B 6/145
250/370.09
8,536,534 B2   9/2013 Okada
(Continued)

FOREIGN PATENT DOCUMENTS

CN    1147752 A    4/1997
CN    102370489 A    3/2012
(Continued)

OTHER PUBLICATIONS

Chinese Office Action and Search Report, dated Jul. 6, 2016, for Chinese Application No. 201380034811.7, including English translation of Chinese Office Action.
(Continued)

*Primary Examiner* — Anastasia Midkiff
(74) *Attorney, Agent, or Firm* — Birch, Stewart, Kolasch & Birch, LLP

(57) ABSTRACT

In an X-ray imaging apparatus, a detection panel has monitor pixels for monitoring X-rays. A signal processor samples a dose signal of a dose per unit time of X-rays according to an output of the monitor pixels. A start detector checks whether irradiation of X-rays is started according to a result of comparison between the dose signal and a start threshold. An AEC device acquires cumulative dose from a start time of the start of irradiation of X-rays until acquisition time after a predetermined time according to the dose signal. According to the cumulative dose, a predicted time point of a reach of the cumulative dose to a target dose is estimated. A stop signal is transmitted to a radiation source controller at the predicted time point, to stop the irradiation of X-rays.

17 Claims, 11 Drawing Sheets

(51) Int. Cl.
*H05G 1/56* (2006.01)
*H05G 1/44* (2006.01)
*A61B 6/00* (2006.01)
A61N 5/10 (2006.01)
H05G 1/38 (2006.01)
H05G 1/32 (2006.01)
H05G 1/34 (2006.01)
H05G 1/42 (2006.01)
G01N 23/04 (2018.01)
H04N 5/32 (2006.01)

(52) U.S. Cl.
CPC .............. *H05G 1/56* (2013.01); *A61B 6/4283* (2013.01); *A61B 6/54* (2013.01); *A61B 2560/0204* (2013.01); *A61B 2560/0266* (2013.01); *A61N 5/1071* (2013.01); *G01N 23/04* (2013.01); *G01N 2223/306* (2013.01); *H04N 5/32* (2013.01); *H05G 1/32* (2013.01); *H05G 1/34* (2013.01); *H05G 1/38* (2013.01); *H05G 1/42* (2013.01)

(58) Field of Classification Search
CPC ............ A61B 2560/00; A61B 2560/02; A61B 2560/0204; A61B 2560/0266; A61N 5/1048; A61N 5/1064; A61N 5/1071; G01T 1/00; G01T 1/02; G01T 1/026; G01T 1/15; G01T 1/16; G01T 1/161; G01T 1/17; G01T 1/20; G01T 1/2006; G01T 1/2018; G01T 1/24; G01T 1/241; G01T 1/244; G01T 1/245; G01T 1/246; G01T 1/247; G01T 7/00; G01T 7/12; H05G 1/00; H05G 1/08; H05G 1/26; H05G 1/28; H05G 1/30; H05G 1/32; H05G 1/34; H05G 1/38; H05G 1/42; H05G 1/44; H05G 1/56
See application file for complete search history.

(56) References Cited

U.S. PATENT DOCUMENTS

2008/0317205 A1* 12/2008 Inuga .................. A61B 6/4441
378/97
2012/0018640 A1* 1/2012 Shimizukawa ........... G01T 1/16
250/354.1
2012/0049077 A1* 3/2012 Okada ............... H01L 27/14603
250/370.08
2012/0305792 A1* 12/2012 Kuwabara ................ G01T 1/17
250/394
2013/0148784 A1* 6/2013 Tajima ..................... H05G 1/42
378/62
2013/0223592 A1* 8/2013 Sato ..................... A61B 6/4233
378/62
2014/0205066 A1* 7/2014 Kitagawa ............... A61B 6/542
378/62

FOREIGN PATENT DOCUMENTS

| EP | 2601891 A1 * | 6/2013 | ............... H05G 1/42 |
| JP | 2010-75556 A | 4/2010 | |
| JP | 2011-172606 A | 9/2011 | |
| JP | 2012-52896 A | 3/2012 | |

OTHER PUBLICATIONS

International Preliminary Report on Patentability and Translation of the Written Opinion of the International Searching Authority (Forms PCT/IB/338, PCT/IB/373 and PCT/ISA/237), dated Dec. 4, 2014, for International Application No. PCT/JP2013/064474.
English translation of the Chinese Second Office Action dated Jan. 5, 2017, for Chinese Application No. 201380034811.7.
Japanese Office Action and English translation thereof, dated Jan. 6, 2016, for counterpart Japanese Application No. 2012-119607.
English Translation of Written Opinion of the International Searching Authority, issued in PCT/JP2013/064474, dated Aug. 27, 2013.
Chinese Office Action, dated Jun. 26, 2017, for corresponding Chinese Application No. 201380034811.7, as well as an English translation.
International Search Report, issued in PCT/JP2013/064474, dated Aug. 27, 2013.
Written Opinion of the International Searching Authority, issued in PCT/JP2013/064474, dated Aug. 27, 2013.

* cited by examiner

| BODY PART | TUBE VOLTAGE | TUBE CURRENT | IRRADIATION TIME | STOP THRESHOLD | ΔT |
|---|---|---|---|---|---|
| ⋮ | ⋮ | ⋮ | ⋮ | ⋮ | ⋮ |
| CHEST | Va | Ia | ta | THa | Ta |
| ABDOMEN | Vb | Ib | tb | THb | Tb |
| ⋮ | ⋮ | ⋮ | ⋮ | ⋮ | ⋮ |

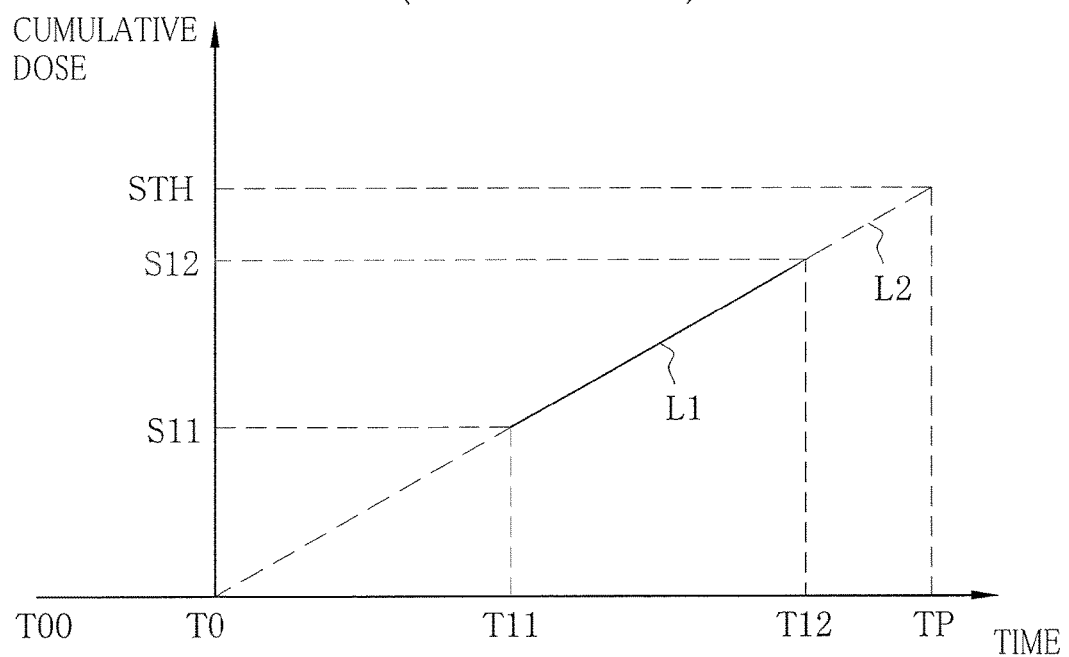

RADIOGRAPHIC IMAGING APPARATUS, METHOD AND SYSTEM

CROSS-REFERENCE TO RELATED APPLICATION

This application is a Continuation of PCT International Application PCT/JP2013/064474 filed on 24 May 2013, which claims priority under 35 USC 119(a) from Japanese Patent Application No. 2012-119607 filed on 25 May 2012. The above application is hereby expressly incorporated by reference, in its entirety, into the present application.

BACKGROUND OF THE INVENTION

1. Field of the Invention

The present invention relates to a radiographic imaging apparatus, method and system. More particularly, the present invention relates to a radiographic imaging apparatus, method and system in which autoexposure control can be performed with precision by monitoring cumulative dose of radiation.

2. Description Related to the Prior Art

An X-ray imaging system is well-known in the medical field in which X-rays are used as radiation. The X-ray imaging system includes an X-ray generating apparatus and an X-ray imaging apparatus. The X-ray generating apparatus generates X-rays. The X-ray imaging apparatus images a body or object receiving X-rays, to form an X-ray image. The X-ray generating apparatus includes an X-ray source and a radiation source controller. The X-ray source emits X-rays toward the body of a patient. The radiation source controller controls operation of the X-ray source. The X-ray imaging apparatus includes a radiographic imaging unit (X-ray imaging unit) such as an electronic cassette, and a console unit. The radiographic imaging unit detects the X-ray image according to the X-rays passed through the body. The console unit controls the radiographic imaging unit, and stores and displays the X-ray image.

The radiographic imaging unit includes a detection panel and a control circuit board. The detection panel, for example, flat panel detector (FPD), detects an X-ray image as electric signal. Pixels are arranged on the detection panel two-dimensionally for storing signal charge according to a dose of X-rays. The control circuit board includes a signal processor and a controller. The signal processor has a switching element and an integrating amplifier. The signal charge is readout from pixels through the switching element, for example, TFT (thin film transistor), stored by the integrating amplifier, and converted into a voltage signal. The signal processor outputs an image signal for constituting the X-ray image.

The controller controls the detection panel in pixel phases of pixel reset, storing and image readout. In the pixel reset, the charge stored in pixels is swept out. In the storing, signal charge is stored in the pixels by turning off the switching element of anyone of the pixels. In the image readout after the storing, the signal charge is read out from a first pixel row to a final pixel row, to output the X-ray image of one frame. In the pixel readout, the signal charge stored in the integrating amplifier is reset (abandoned) at each time of outputting the image signal of one row according to the signal charge, so as to be ready for storing of signal charge of next pixel row.

The pixel reset is to sweep out unwanted stored charge of pixels due to dark current charge irrespective of irradiation of X-rays or residual charge of previous imaging, so as to minimize influence of noise to an X-ray image. The controller drives the detection panel to perform the pixel reset repeatedly before starting irradiation of X-rays. It is necessary in the radiographic imaging unit to synchronize a start of irradiation of X-rays in the X-ray generating apparatus with a start of the storing upon terminating the pixel reset. To this end, a sync signal is transmitted between the X-ray generating apparatus and the radiographic imaging unit. In the radiographic imaging unit, the detection panel is triggered by the sync signal to change over from the pixel reset to the storing.

U.S. Pat. No. 8,536,534 (corresponding to U.S. Pat. Pub. 2012/049,077 and JP-A 2010-052896) and JP-A 2010-075556 disclose an example of the radiographic imaging unit having an AEC device (automatic exposure control device) for automatically controlling exposure of the X-ray image for obtaining appropriate image quality and minimizing exposure of radiation to the body or object. The radiographic imaging unit includes a radiation monitoring device and a dose sampler. The radiation monitoring device detects X-rays incident upon the detection panel. The dose sampler samples a dose signal representing a dose of X-rays per unit time according to an output of the radiation monitoring device. An example of the radiation monitoring device is partial monitor pixels included in the pixels of the detection panel. An example of the dose sampler is a signal processor for reading out the signal charge from the pixels. The dose sampler includes an integrating amplifier, which stores the charge output by the radiation monitoring device according to the dose, and outputs a voltage signal as a dose signal according to the stored charge. The dose signal is sampled at a predetermined sampling period corresponding to a period of storing the charge in the integrating amplifier.

The AEC device acquires a cumulative dose of X-rays according to the dose signal, and checks whether the cumulative dose has become equal to a predetermined target dose. The radiographic imaging unit changes over from the storing to the readout upon the reach of the cumulative dose to the target dose.

U.S. Pat. No. 8,536,534 discloses the radiographic imaging unit having a function of detecting a start of irradiation of X-rays according to a sampled dose signal in the dose sampler, for auxiliary effect in a structure without a communication path to the radiation source controller. In the radiographic imaging unit, dose sampling is started before starting the irradiation of X-rays. The start of the irradiation is detected according to a result of comparison between the sampled dose signal and a predetermined start threshold (turn-on threshold). The storing is started immediately after the start detection.

Also, JP-A 2010-075556 discloses the radiographic imaging unit in which a predicted time point of a reach of the cumulative dose to the target dose is estimated according to a metered dose or the cumulative dose earlier than a reach to the target dose instead of acquiring the cumulative dose until the reach of the cumulative dose to the target dose. An AEC device stops irradiation of X-rays at the predicted time point.

To estimate the predicted time point requires acquisition of changes in the cumulative dose with time. In the radiographic imaging unit of JP-A 2010-075556, the cumulative dose is acquired at two time points during the irradiation of X-rays. The predicted time point is estimated for a reach of the cumulative dose to the target dose by use of linear extrapolation from the cumulative dose of the two time points. In FIG. 13, the radiographic imaging unit acquires a metered dose S11 as the cumulative dose at acquisition time T11 upon lapse of a predetermined period from a reception time T00 of receiving a sync signal from the radiation source controller, according to the sampled dose signal from the dose sampler. Furthermore, a metered dose S12 is acquired at the acquisition time T12 upon lapse of the predetermined period from the acquisition time T11. Then an interpolation line L1 is plotted by linear connection between the metered dose S11 at the acquisition time T11 and the metered dose S12 at the acquisition time T12. An extrapolation line L2 is formed by extension of the interpolation line L1 from the acquisition time T12. A time point at which the extrapolation line L2 reaches the target dose is obtained as the predicted time point.

However, a problem arises with the estimation of the predicted time point TP in the radiographic imaging unit of JP-A 2010-075556. In the X-ray generating apparatus, X-rays are not applied to the radiographic imaging unit at the same time as the radiographic imaging unit receives the sync signal. A time lag occurs from reception time T00 to a start time T0 at which X-rays are applied to the radiographic imaging unit. The time lag differs with various conditions, for example, a fine difference in manual operation of an operator, specificity or specifications of the X-ray source as a product, imaging condition, degradation of the X-ray source with time, and the like. Dosimetry of the cumulative dose in a first event during the time lag is not useful because no X-rays are emitted during the time lag.

Thus, it is necessary to perform the dosimetry of the first event by considering the time lag from the time T0 for the reliability in the dosimetry during irradiation of X-rays after the start time T0. However, the time lag may change with various conditions. The acquisition time T11 must be determined by expecting a longest value of the time lag for safety in all of the various conditions. However, the acquisition time T11 of the dosimetry of the first event is considerably later than the start time T0. At least two time points for the cumulative dose are required for estimating the predicted time point TP. The acquisition time T12 of a second event becomes late in compliance with the delay of the acquisition time T11. A problem arises in considerable waiting time required for obtaining the predicted time point.

Should an interval be too short between the acquisition times T11 and T12, reliability of the estimation of the predicted time point TP may be low. Thus, the interval between the acquisition times T11 and T12 should be sufficiently long. However, the estimation of the predicted time point TP will take long time according to the greatness of the interval between the acquisition times T11 and T12. A serious problem may occur in that the cumulative dose may reach the target dose before terminating the estimating the predicted time point TP so that longer time may pass than is enough for irradiation of X-rays. The body or object is likely to receive unwanted irradiation. The estimation of the predicted time point will be inappropriate for imaging of a low dose with a short irradiation time, because a dose of X-rays is kept low for the imaging.

SUMMARY OF THE INVENTION

In view of the foregoing problems, an object of the present invention is to provide a radiographic imaging apparatus, method and system in which autoexposure control can be performed with precision by monitoring cumulative dose of radiation.

In order to achieve the above and other objects and advantages of this invention, a radiographic imaging apparatus is provided, and includes a detection panel, having plural pixels, for detecting dose of radiation of an object irradiated with radiation by a radiation generating apparatus, for storing signal charge according thereto, and for outputting an image signal of a radiation image of the object. A radiation monitoring device monitors the radiation incident upon the detection panel. A dose sampler samples a dose signal of the dose of the radiation per unit time according to an output of the radiation monitoring device. A start detector detects a start of irradiation of the radiation from the radiation generating apparatus according to comparison of the dose signal with a predetermined start threshold. An autoexposure control device acquires cumulative dose of the radiation according to the dose signal from a start time of the detected start from the start detector until acquisition time, estimates a predicted time point of reach of the cumulative dose to a stop threshold according to the start time and the acquisition time, and stops the irradiation of the radiation from the radiation generating apparatus at the predicted time point.

Preferably, the autoexposure control device obtains a correlation of the cumulative dose to elapsed time according to the cumulative dose at the start time and the acquisition time, and acquires the predicted time point corresponding to the stop threshold by performing extrapolation according to the correlation.

Preferably, the dose sampler outputs the dose signal by sampling of one event from the start time.

Preferably, the dose sampler includes an integrating amplifier for storing charge output by the radiation monitoring device, and outputting the dose signal according to the stored charge.

Preferably, a first sampling period of sampling the dose signal from the start time is set equal to a length from the start time to the acquisition time by the dose sampler.

Preferably, the dose sampler samples the dose signal at a second sampling period shorter than the first sampling period before the start time, and changes over sampling to the first sampling period at the start time.

Preferably, the autoexposure control device outputs a control signal for stopping the irradiation of the radiation generating apparatus at the predicted time point.

Preferably, the control signal is a stop signal, output at the predicted time point, for stopping the radiation generating apparatus for the irradiation.

In another preferred embodiment, the control signal is a signal of the predicted time point or a signal of remaining time until the predicted time point.

Preferably, assuming that the cumulative dose after the start time is equal to or lower than a lower limit, the autoexposure control device acquires a cumulative dose again to estimate the predicted time point.

Preferably, the first sampling period is changeable according to a body part of the object.

Preferably, the radiation monitoring device is constituted by at least part of the pixels.

Preferably, the pixels include normal pixels for receiving the radiation and outputting the signal charge to a signal line. Monitor pixels constitute the radiation monitoring device and output charge discretely from the normal pixels.

In one preferred embodiment, furthermore, a signal processor reads out the signal charge from the pixels and constituting the dose sampler.

Preferably, the detection panel is a portable electronic cassette.

Also, a radiographic imaging method of detecting a radiation image of an object by use of a detection panel is provided, the detection panel having plural pixels, for detecting dose of radiation of the object irradiated with radiation by a radiation generating apparatus, for storing signal charge according thereto, and for outputting an image signal of the radiation image of the object. In the radiographic imaging method, the radiation incident upon the detection panel is monitored. A dose signal of the dose of the radiation per unit time is sampled according to a result of monitoring the radiation. A start of irradiation of the radiation from the radiation generating apparatus is detected according to comparison of the dose signal with a predetermined start threshold. Cumulative dose of the radiation is acquired according to the dose signal from a start time of the detected start of the irradiation until acquisition time. A predicted time point of reach of the cumulative dose to a stop threshold according to the start time and the acquisition time is estimated. The irradiation of the radiation from the radiation generating apparatus is stopped at the predicted time point.

Also, a radiographic imaging system including a radiation generating apparatus for emitting radiation and a radiographic imaging apparatus for detecting a radiation image of an object is provided. The radiographic imaging apparatus includes a detection panel, having plural pixels, for detecting dose of radiation of the object irradiated with the radiation by the radiation generating apparatus, for storing signal charge according thereto, and for outputting an image signal of the radiation image of the object. A radiation monitoring device monitors the radiation incident upon the detection panel. A dose sampler samples a dose signal of the dose of the radiation per unit time according to an output of the radiation monitoring device. A start detector detects a start of irradiation of the radiation from the radiation generating apparatus according to comparison of the dose signal with a predetermined start threshold. An autoexposure control device acquires cumulative dose of the radiation according to the dose signal from a start time of the detected start from the start detector until acquisition time, estimates a predicted time point of reach of the cumulative dose to a stop threshold according to the start time and the acquisition time, and stops the irradiation of the radiation from the radiation generating apparatus at the predicted time point.

Consequently, autoexposure control can be performed with precision by monitoring cumulative dose of radiation, because a predicted time point for appropriate exposure can be acquired and utilized.

BRIEF DESCRIPTION OF THE DRAWINGS

The above objects and advantages of the present invention will become more apparent from the following detailed description when read in connection with the accompanying drawings, in which:

FIG. 13 is a graph illustrating a known method of estimating a predicted time point according to the prior art.

DETAILED DESCRIPTION OF THE PREFERRED EMBODIMENT(S) OF THE PRESENT INVENTION

Figure 1:
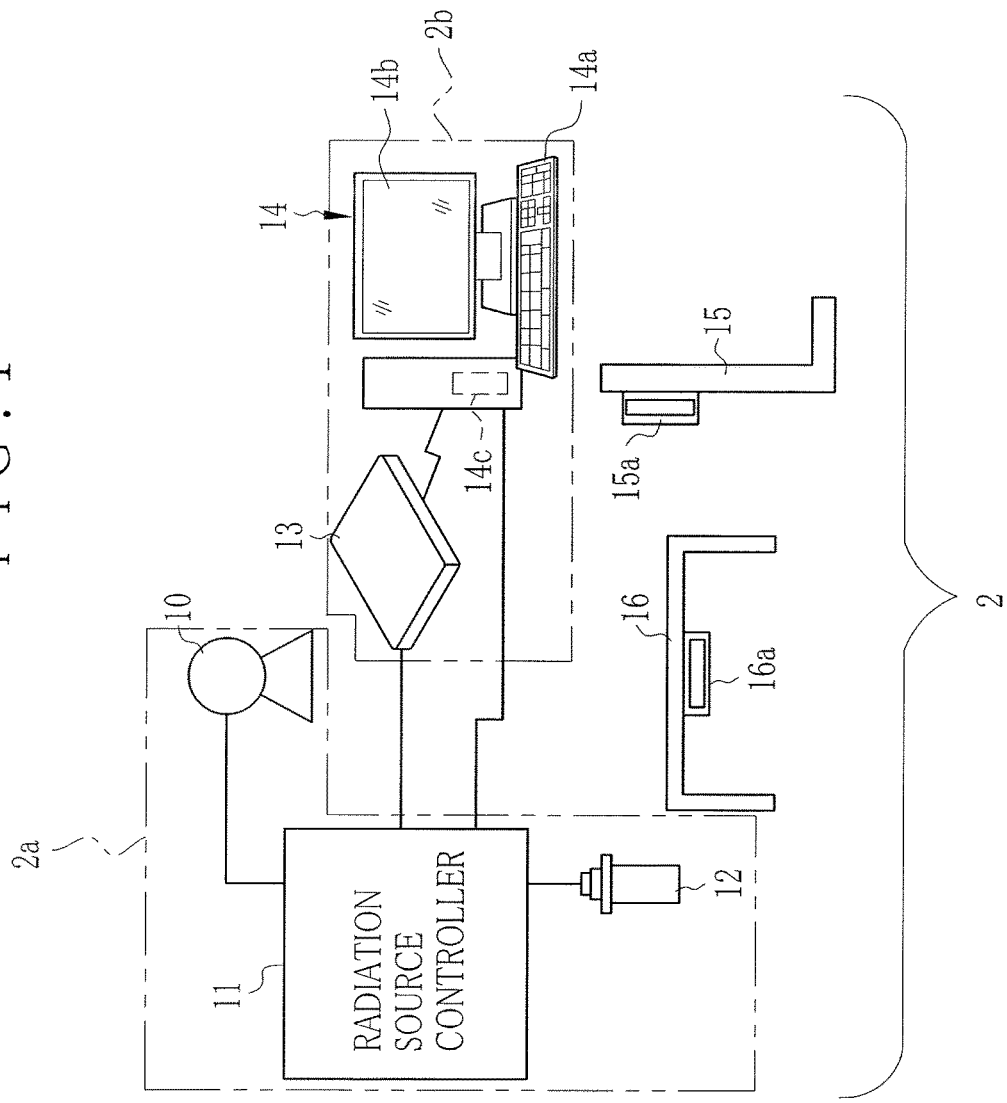
FIG. 1 is an explanatory view illustrating an X-ray imaging system.

In FIG. 1, an X-ray imaging system 2 as radiographic imaging system includes an X-ray generating apparatus 2a (radiation generating apparatus), and an X-ray imaging apparatus 2b (radiographic imaging apparatus). The X-ray generating apparatus 2a includes an X-ray source 10, a radiation source controller 11 (source driver) and a radiation switch 12. The X-ray source 10 has an X-ray tube incorporated therein, for emitting X-rays. The X-ray imaging apparatus 2b includes an electronic cassette 13 and a console unit 14. The electronic cassette 13 is a portable radiographic imaging unit, and outputs an X-ray image by detecting X-rays transmitted through a body of a patient. The console unit 14 controls operation of the electronic cassette 13 for storing the X-ray image and displaying the same. The electronic cassette 13 includes an AEC function for outputting an AEC signal to stop the X-ray generating apparatus 2a from emitting X-rays, so as to control the exposure of the X-ray image.

The electronic cassette 13 is mounted removably to a cassette holder 15a of a standing orientation imaging station 15 (floor stand), or to a cassette holder 16a of a horizontal orientation imaging station 16 (imaging table). The standing orientation imaging station 15 is used for imaging a body in a standing orientation. The horizontal orientation imaging station 16 is used for imaging a body in a horizontal orientation. The electronic cassette 13 is secured to the cassette holder 15a or 16a of the imaging station 15 or 16 in an orientation of directing a front wall 34a (see FIG. 3) to the X-ray source 10. The body is positioned by an operator such as a radiologist to locate a body part between the X-ray source 10 and the electronic cassette 13. The X-ray source 10 is settable in a desired direction and position by use of a source moving mechanism (not shown), and is used commonly by the imaging stations 15 and 16.

The console unit 14 is connected to the electronic cassette 13 communicably in a wired manner or wirelessly. The console unit 14 includes a user input interface 14a, a display 14b and a storage medium 14c. The user input interface 14a, for example, keyboard, mouse and other input devices, receives an imaging condition and other information from an operator. The display 14b displays an X-ray image from the electronic cassette 13, and an input screen for the imaging condition and the like. The storage medium 14c is a hard disk drive or the like, and stores X-ray images from the electronic cassette 13 and various data required for X-ray imaging. Note that an image server (not shown) can be used in connection with the console unit 14 by the network, for storing an X-ray image.

The console unit 14 receives an input of an imaging request having information of sex and age of the body H, and body parts such as head, chest, abdomen, hand, fingers and the like. The display 14b is driven to display the imaging request. An external managing system (not shown) for managing object information and imaging information of radiographic imaging is connected to the console unit 14 and inputs the imaging request. Examples of the external managing system are the HIS (hospital information system) and the RIS (radiology information system). Also, it is also possible for a physician or operator manually to input the imaging request by use of the user input interface 14a.

The X-ray source 10 includes an X-ray tube and a collimator. The X-ray tube emits X-rays. The collimator limits a field of irradiation of X-rays from the X-ray tube. The X-ray tube includes a negative electrode and a positive electrode. The negative electrode is a filament for emitting thermal electron. The positive electrode is a target receiving collision of the thermal electron, and emits X-rays. The collimator is constituted by four movable plates of metal lead arranged quadrilaterally for blocking X-rays. An emission opening of a quadrilateral shape is defined in the collimator at the center for transmitting X-rays. The movable plates are moved to adjust the size of the emission opening, to change the field of irradiation.

Figure 2:
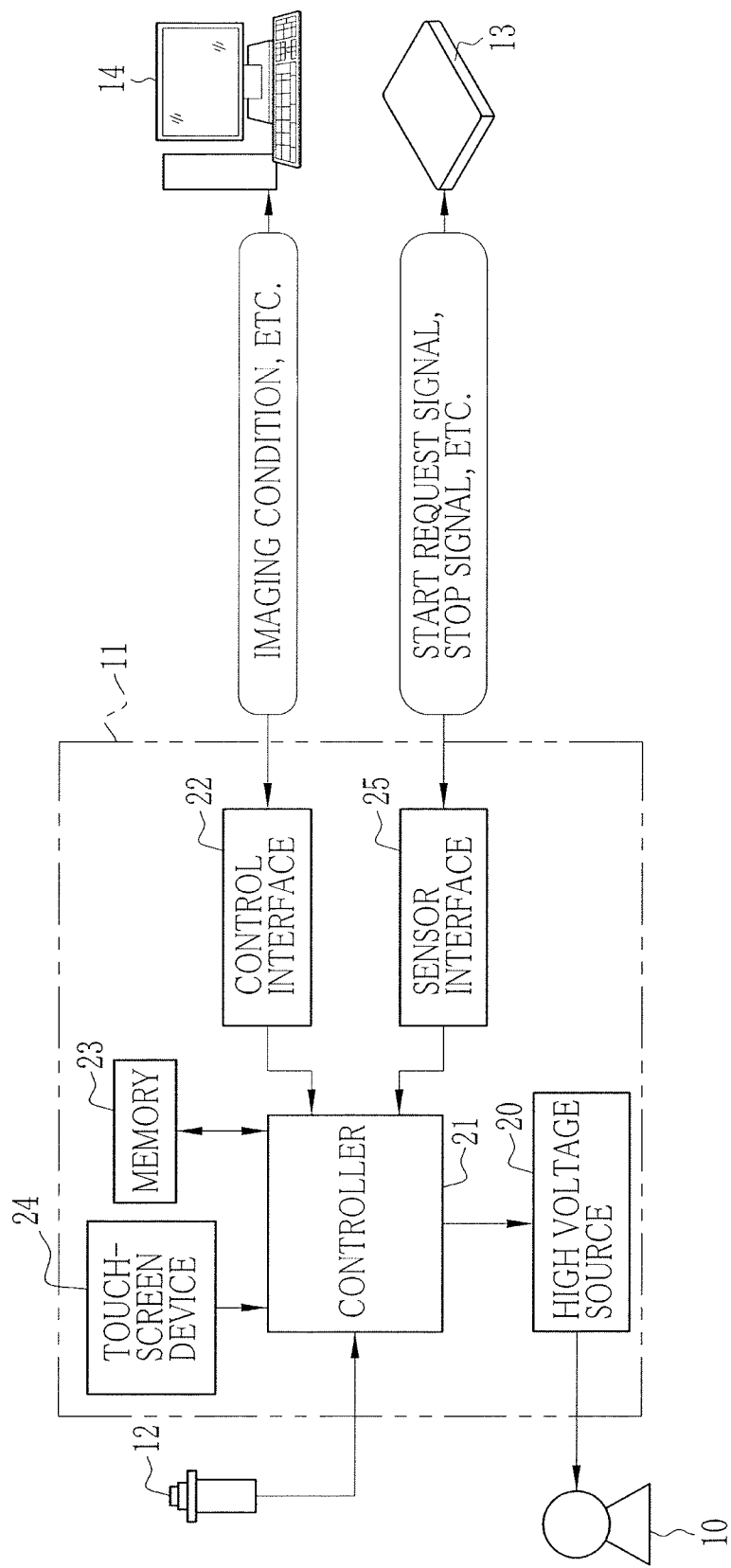
FIG. 2 is a block diagram schematically illustrating a radiation source controller.

As illustrated in FIG. 2, the radiation source controller 11 includes a high voltage source 20, a controller 21 and a control interface 22 (I/F) or communication interface. The high voltage source 20 generates a tube voltage of a high level by boosting an input voltage with a transformer, and supplies the tube voltage to the X-ray source 10 through a high voltage cable. The controller 21 controls operation of the high voltage source 20. The control interface 22 is used to transmit or receive information and signals in connection with the console unit 14.

Various elements are connected to the controller 21, including the radiation switch 12, a memory 23, a touchscreen device 24 or touch panel, and a sensor interface 25 (T/F) or irradiation signal interface. The radiation switch 12 is a two-step switch operable manually by a physician or operator. The radiation switch 12, upon being depressed at a first step, generates a warmup start signal for staring warmup of the X-ray source 10, and upon being depressed at a second step, generates a turn-on signal for starting irradiation of the X-ray source 10. The warmup start signal and turn-on signal are input to the controller 21 by a signal cable.

The touchscreen device 24 is operated by an operator for inputting an irradiation condition of X-rays. Information of the irradiation condition includes a tube voltage, tube current and irradiation time. The tube voltage determines an energy spectrum of X-rays from the X-ray source 10. The tube current determines a dose of radiation per unit time. The irradiation time is time of applying the tube voltage for irradiation. The controller 21 controls the tube voltage of the high voltage source 20, tube current and irradiation time according to the irradiation condition input by the touchscreen device 24.

The sensor interface 25 is connected to the electronic cassette 13 in a wired manner or wirelessly, and communicates with the electronic cassette 13 for a sync signal. The sync signal synchronizes a start of irradiation of X-rays in the X-ray generating apparatus 2a. Examples of the sync signal are a start request signal and an enable signal. The start request signal from the radiation source controller 11 is for allowance of a start of irradiation of X-rays in the electronic cassette 13, and is transmitted by the sensor interface 25 to the electronic cassette 13 before starting the irradiation. The enable signal is transmitted by the electronic cassette 13 to the radiation source controller 11 upon completing the preparation for receiving irradiation of the electronic cassette 13.

Irradiation of X-rays from the X-ray generating apparatus 2a is not started shortly after the transmission of a start request signal or enable signal in the sensor interface 25. There occurs a time lag between the transmission of the enable signal and actual irradiation of X-rays (see FIG. 5 with reception time T00 and start time T0). The time lag is different according to a fine difference in manual operation of an operator, specificity or specifications of the X-ray source as a product, imaging condition, degradation of the X-ray source with time, and the like.

The sensor interface 25 is also used for transmitting a stop signal from the electronic cassette 13 to the radiation source controller 11. The stop signal is an AEC signal for immediately stopping irradiation of the X-ray generating apparatus 2a in the use of the AEC of the electronic cassette 13. The stop signal is output in case it is judged that the cumulative dose of X-rays has become equal to the target dose in the electronic cassette 13. The sensor interface 25 receives the enable signal and stop signal, and inputs those to the controller 21.

In case a warmup start signal is input by the radiation switch 12, the controller 21 drives the high voltage source 20 to start warming up the X-ray source 10. A predetermined voltage is applied to the filament of the X-ray source 10 for preheating. Its target starts being rotated simultaneously. The warmup is terminated in case preheating of the filament is terminated and the target comes to rotate at a predetermined rate.

In case the sensor interface 25 receives the enable signal from the electronic cassette 13 and receives the turn-on signal from the radiation switch 12, the controller 21 actuates the high voltage source 20 to start irradiation of X-rays in the X-ray source 10. In case the sensor interface 25 receives the stop signal from the electronic cassette 13, the controller 21 controls the high voltage source 20 to stop the X-ray source 10 from irradiation of X-rays.

The memory 23 stores a plurality of data of irradiation conditions, inclusive of a tube voltage, tube current, irradiation time, current/time product of the tube current and irradiation time (or mAs value), and the like. One of the irradiation conditions is manually set by an operator by use of the touchscreen device 24. The radiation source controller 11 emits X-rays according to the irradiation condition being set. Assuming that the stop signal is received, the radiation source controller 11 stops the irradiation of X-rays even in case the irradiation time or the current/time product is smaller than its target value. Also, the target value of the irradiation time or the current/time product is predetermined at a sufficiently high level in the radiation source controller 11 so as to prevent termination of the irradiation before reception of a stop signal in the condition of using the AEC function. For example, the irradiation time is set at the maximum irradiation time according to regulation of safety at preset levels for body parts for the purpose of preventing excessive exposure of radiation to the human body.

A timer (not shown) is incorporated in the controller 21 for staring measuring time upon start of the irradiation of X-rays. The controller 21 stops the irradiation of X-rays in case the measured time in the timer becomes the irradiation time in the irradiation condition without receiving a stop signal in the sensor interface 25, or in case the measured time becomes the maximum irradiation time in the radiation source controller 11 in view of the safety regulation. Those events are similar to reception of the stop signal in the sensor interface 25.

Figure 3:
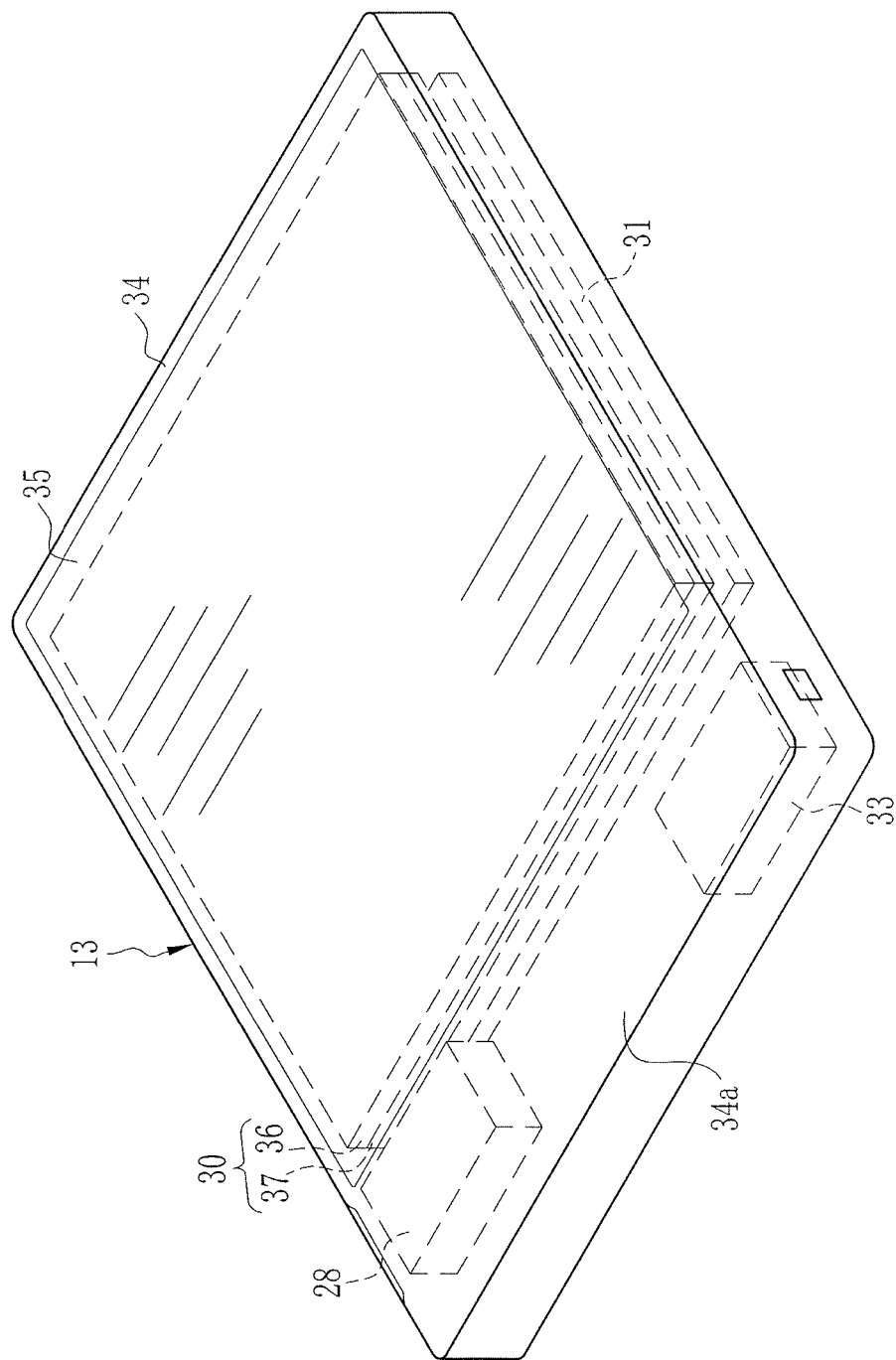
FIG. 3 is a perspective view illustrating an electronic cassette.

In FIG. 3, the electronic cassette 13 includes a detection panel 30, a control circuit board 31, a battery 28, a communication interface 33, and a portable housing 34 for containing those elements. The portable housing 34 is a substantially quadrilateral form of a small thickness, and is formed from, for example, electrically conductive resin. A quadrilateral opening is formed in the front wall 34a of the portable housing 34 for entry of X-rays. A radio transparent plate 35 is secured to the opening as a top wall. The radio transparent plate 35 is formed from carbon material having a small weight, high rigidity and high radio transparency to X-rays. An area size of the portable housing 34 is the same as that of a film cassette and IP cassette (CR cassette) according to the International Standards ISO 4090:2001. Thus, the electronic cassette 13 can be mounted on a known imaging station for use with a film cassette and IP cassette.

A plurality of the electronic cassettes 13 are placed in one examination room where the X-ray imaging system 2 is installed, for example, two for the imaging stations 15 and 16. Before the imaging, one of the two is selected by use of the console unit 14. Various methods of placing the electronic cassette 13 for imaging are usable. The electronic cassette 13 can be set on the imaging station 15 or 16, placed on a bed where the body lies, and manually held by hands of the patient (body). The electronic cassette 13 can be used in a discrete manner.

The battery 28 causes a power source circuit (not shown) to supply various elements with power in the electronic cassette 13. The battery 28 for use is a relatively small type containable in the portable housing 34 of a small thickness. The battery 28 is removable from the portable housing 34, and is chargeable by a special charger (not shown). It is possible to construct the battery 28 in a manner wirelessly chargeable as mounted in the electronic cassette 13.

The communication interface 33 is connected with the radiation source controller 11 and the console unit 14 in a wired manner or wirelessly, and transmits and receives information in connection with the radiation source controller 11 and the console unit 14, for example, the above-described sync signal, imaging condition, X-ray images and the like. Assuming that wireless communication between the electronic cassette 13 and the console unit 14 is impossible due to shortage in remaining power of the battery 28 or the like, the communication interface 33 becomes connected with the console unit 14 in a wired manner. A cable from the console unit 14 to the communication interface 33 enables the wired communication with the console unit 14. Also, it is possible to supply the electronic cassette 13 with power from a power source of the console unit 14.

The detection panel 30 includes scintillator 36 (phosphor) and a photoconductive plate 37 or photo detection board. The scintillator 36 and the photoconductive plate 37 are arranged in this order in a travel direction of X-rays or direction of the entry. The scintillator 36 contains phosphor components such as thallium activated cesium iodide (CsI: Tl), and GOS or terbium activated gadolinium oxysulfide ($Gd_2O_2S$:Tb), and converts the incident X-rays from the radio transparent plate 35 into visible light for output.

The photoconductive plate 37 detects visible light emitted by the scintillator 36, and converts the light into an electric signal. The control circuit board 31 controls the photoconductive plate 37, and generates an X-ray image according to the electric signal from the photoconductive plate 37. It is possible to arrange the scintillator 36 and the photoconductive plate 37 in the travel direction of X-rays, namely according to the arrangement of the penetration side sampling (PSS), or arrange the photoconductive plate 37 and the scintillator 36 in a direction opposite to the travel direction of X-rays, namely according to the arrangement of the irradiation side sampling (ISS). Also, the scintillator 36 may not be formed. It is possible to use a detection panel of a direct conversion type having a conversion layer of amorphous selenium or the like for directly converting X-rays into electric charge without the scintillator 36.

Figure 4:
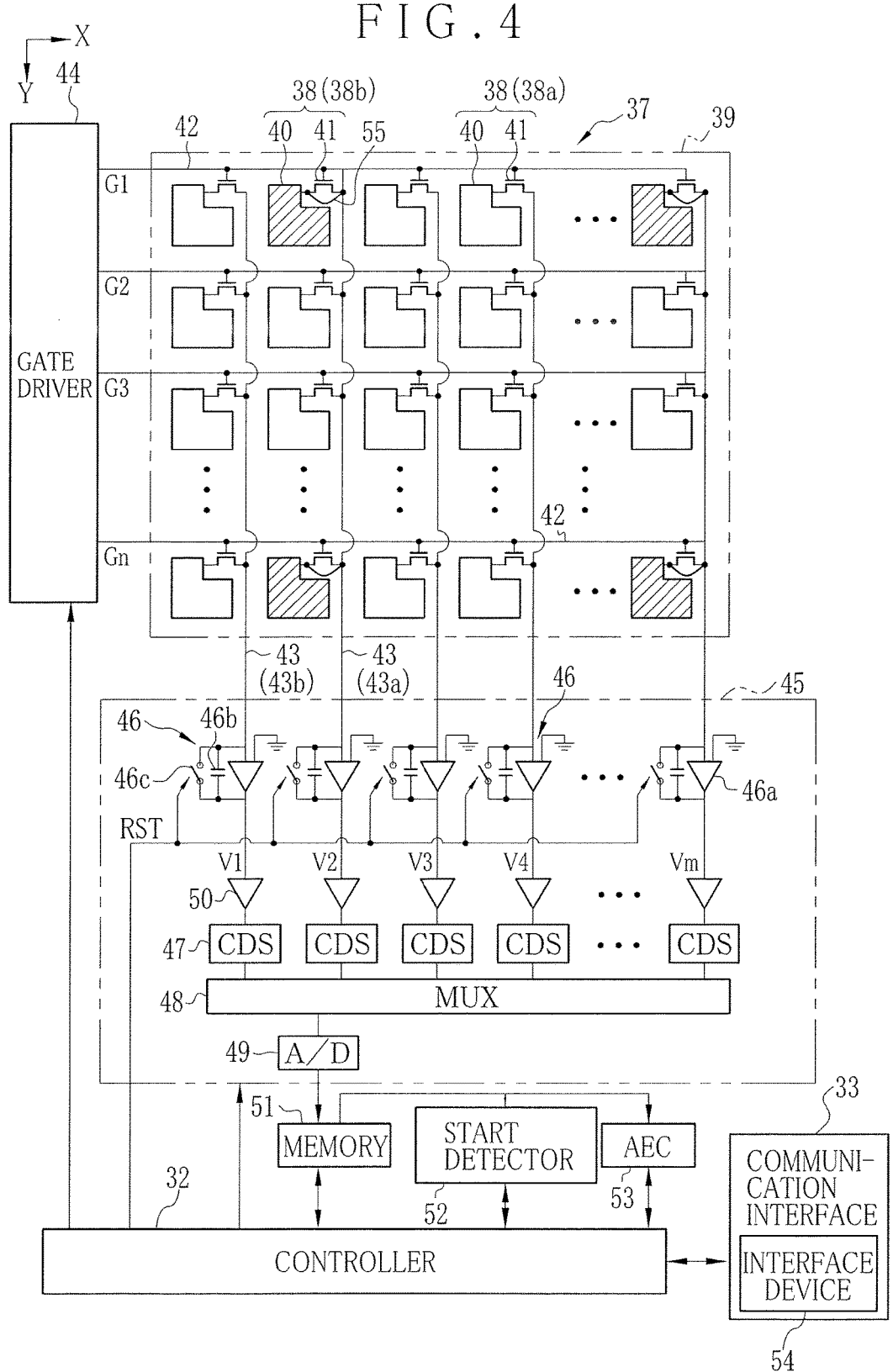
FIG. 4 is a block diagram schematically illustrating the electronic cassette.

In FIG. 4, the photoconductive plate 37 includes an imaging surface 39 constituted by plural pixels 38 arranged on a glass substrate (not shown) for storing charge according to a dose of X-rays. The pixels 38 are arranged in a matrix form of n rows (in the X direction) and m columns (in the Y direction) in a two-dimensional manner at a predetermined pitch. Note that n and m are integers equal to or more than 2, for example, are nearly equal to 1,024. The pixels 38 can be arranged in a manner different from the regular rectangular arrangement, for example, a honeycomb arrangement.

Each of the pixels 38 includes a photo diode 40 and a TFT 41 (thin film transistor) as a switching element. The photo diode 40 is a photoconductor for generating charge (electron-hole pair) upon receiving visible light, and storing the charge.

The photo diode 40 includes a semiconductor layer (for example, p-intrinsic-n (PIN) type), and upper and lower electrodes formed thereon. The semiconductor layer generates charge. The TFT 41 is connected to the lower electrode. A bias line is connected to the upper electrode. The number of the bias lines is n as the number of the rows of the pixels 38. The bias lines are connected to one bus line. The bus line is connected to a bias power source. The bias power source applies the bias voltage to the upper electrode of the photo diode 40 through the bus line and the bias lines. Thus, an electric field is created within the semiconductor layer by the bias voltage. The photo diode 40 is used in a reversely biased state. Electrons of charge (electron-hole pairs) generated in the semiconductor layer by the photoelectric conversion move to the upper electrode and become absorbed by the bias lines. The hole moves to the lower electrode and is collected as signal charge.

Each of the TFTs 41 has a gate, source and drain. The gate is connected to one of scan lines 42. The source is connected to one of signal lines 43. The drain is connected to the lower electrode of the photo diode 40. The scan lines 42 are extended in the X direction or row direction of the pixels 38, and arranged at a predetermined pitch in the Y direction or columnar direction of the pixels 38. The signal lines 43 are extended in the Y direction, and arranged at a predetermined pitch in the X direction. The scan lines 42 and the signal lines 43 are arranged in a grating shape on the imaging surface 39. The pixels 38 are disposed at points of intersection between the scan lines 42 and the signal lines 43. The number of the scan lines 42 is n as the number of rows of the pixels 38. The number of the signal lines 43 is m as the number of columns of the pixels 38. The scan lines 42 are connected to a gate driver 44. The signal lines 43 are connected to a signal processor 45.

The pixels 38 are constituted by normal pixels 38a and monitor pixels 38b (detection pixels). The normal pixels 38a are used for forming an X-ray image. The monitor pixels 38b monitor a dose (intensity) of X-rays incident upon the imaging surface 39 per unit time (corresponding to a radiation monitoring device), perform dosimetry, and are used for detecting a start of the irradiation and for the AEC. The TFT

41 of the monitor pixels 38*b* has a source electrode and a drain electrode which are short-circuited by a short-circuit line 55. Note that the TFT 41 of the normal pixels 38*a* is not short-circuited. In the drawing, the monitor pixels 38*b* are hatched for distinction from the normal pixels 38*a*.

The TFTs 41 in the monitor pixels 38*b* are turned on always irrespective of voltage applied to the gate electrode, because of short-circuiting between the source and drain electrodes. The collected charge at the lower electrode of the photo diode 40 comes to flow out to the signal lines 43 through the short-circuit line 55. In the normal pixels 38*a*, the charge is read out to the signal lines 43 according to the applied voltage of the gate electrode of the TFT 41.

In the monitor pixels 38*b*, the normal pixels 38*a* having the photo diode 40 are repeated but with a difference in that the source and drain electrodes of the TFT 41 are short-circuited. The normal pixels 38*a* and the monitor pixels 38*b* can be manufactured in the same manufacturing process. Note that the monitor pixels 38*b* may be constituted without the TFT 41 by directly connecting the photo diode 40 to the signal lines 43. In the present embodiment, the TFT 41 for the monitor pixels 38*b* is prepared in the same manner as the normal pixels 38*a*, and then the short-circuit line 55 short-circuits the source and drain electrodes to constitute the monitor pixels 38*b*, because it is preferable not to provide a difference in the structure and characteristic between the normal pixels 38*a* and the monitor pixels 38*b*.

The number of the monitor pixels 38*b* is so small that a proportion of the number of all the pixels 38 to that of the monitor pixels 38*b* is from several hundreds to several millions. The signal lines 43 include first signal lines 43*a* and second signal lines 43*b*. The monitor pixels 38*b* are connected to the first signal lines 43*a*. Only the normal pixels 38*a* are connected to the second signal lines 43*b*. The first signal lines 43*a* are arranged cyclically so that plural lines included in the second signal lines 43*b* are positioned between the first signal lines 43*a*. Let the pixels 38 be arranged in a matrix form of 1,024×1,024. 16 of the monitor pixels 38*b* are arranged regularly for each of eight of the signal lines 43 each of which is associated with a group of 128 pixel columns. The number of the monitor pixels 38*b* is 8,192, of which a ratio in the pixels 38 is approximately 0.01%.

The monitor pixels 38*b* are arranged on the imaging surface 39 with discreteness from one another. So any one of the monitor pixels 38*b* can monitor X-rays even assuming that an irradiation area of X-rays is limited to a portion of the imaging surface 39. The positions of the monitor pixels 38*b* are known at the time of manufacture of the detection panel 30. In the electronic cassette 13, an internal memory in a controller 32 previously stores X and Y coordinates of all the monitor pixels 38*b*. Note that arrangement of the monitor pixels 38*b* can be changed suitably. In contrast with the embodiment, the monitor pixels 38*b* can be arranged in a locally concentrated manner. For example, the monitor pixels 38*b* in a mammography apparatus for imaging of breasts can be arranged on sides of breast walls in a concentrated manner.

The control circuit board 31 includes the gate driver 44, the signal processor 45, a memory 51, a start detector 52, an AEC device 53 or autoexposure control device, and the controller 32 for controlling those elements. The controller 32 causes the gate driver 44 to drive the TFT 41, so that the detection panel 30 operates in pixel phases of storing, image readout and pixel reset. In the storing, the detection panel 30 causes the normal pixels 38*a* to store signal charge according to a dose of X-rays. In the image readout, the signal charge is read out of the normal pixels 38*a*. In the pixel reset, dark current charge is read out of the normal pixels 38*a* for abandonment or resetting.

In the storing, no gate pulse is supplied by the gate driver 44 to the scan lines 42. The TFT 41 of the normal pixels 38*a* is turned off, while the normal pixels 38*a* store signal charge. In the image readout and pixel reset, the gate driver 44 sequentially generates gate pulses G1-Gn at a predetermined interval Δt (FIG. 5) for driving the TFTs 41 of a common row, to enable the scan lines 42 one row after another. The TFTs 41 in the normal pixels 38*a* are turned on one row after another in connection with the scan lines 42. The time of turning on the TFT 41 is determined by the pulse width of the gate pulses, so that the TFT 41 becomes turned off again upon the lapse of the time according to the pulse width. Charge stored in the normal pixels 38*a* is read out to the signal lines 43 upon turning on the TFT 41, and input to the signal processor 45.

The signal processor 45 includes an integrating amplifier 46, a CDS circuit 47 (correlated double sampler), a multiplexer 48 (MUX) and an A/D converter 49. The integrating amplifier 46 is connected to each of the signal lines 43 in a discrete manner. The integrating amplifier 46 includes an operation amplifier 46*a* (amplifier device), a capacitor 46*b* and a reset switch 46*c*. The capacitor 46*b* is connected between input and output terminals of the operation amplifier 46*a*. The reset switch 46*c* is connected in parallel with the capacitor 46*b*. The signal lines 43 are connected to one of the input terminals of the operation amplifier 46*a*. A remaining input terminal of the operation amplifier 46*a* is grounded (GND). The integrating amplifier 46 accumulates input charge from the signal lines 43 by storing in the capacitor 46*b*, and converts the accumulated charge into analog voltage signals V1-Vm for output. The reset switch 46*c* is controlled by the controller 32. Turning on the reset switch 46*c* resets or abandons the stored charge in the capacitor 46*b*. An amplifier 50 is combined with the operation amplifier 46*a* of each column. The multiplexer 48 is connected to the output terminal of the operation amplifier 46*a* by the amplifier 50 and the CDS circuit 47. The A/D converter 49 is connected to an output terminal of the multiplexer 48.

The amplifier 50 amplifies the voltage signal of the analog form from the integrating amplifier 46 at a predetermined gain value. The gain value is set by the controller 32 according to the imaging condition from the console unit 14.

The CDS circuit 47 is connected to an output terminal of the amplifier 50, and performs the correlation double sampling to the voltage signal amplified by the amplifier 50, to eliminate reset noise of the integrating amplifier 46 from the voltage signal, and to hold the voltage signal in a predetermined period (sample-hold). To be precise, the CDS circuit 47 includes first and second sample-hold circuits (not shown), and one differential circuit (not shown). The first sample-hold circuit samples and holds the voltage signal output by the amplifier 50. The second sample-hold circuit samples and holds a component of the reset noise of the integrating amplifier 46 output by the amplifier 50 upon resetting of the integrating amplifier 46. The differential circuit obtains a difference between their outputs, to obtain the voltage signal after eliminating the noise.

The multiplexer 48 is connected to outputs of the CDS circuits 47, and includes electronic switches. In response to a control signal from a shift register (not shown), the multiplexer 48 selects the CDS circuits 47 of first to mth columns one after another with the electronic switches. Voltage signals V1-Vm are output from the CDS circuits 47 being selected, and are transmitted to the A/D converter 49 serially by the multiplexer 48. The A/D converter 49 converts the voltage signals V1-Vm into digital voltage signals, which are output to the memory 51. Furthermore, an amplifier can be provided between the multiplexer 48 and the A/D converter 49.

Figure 5:
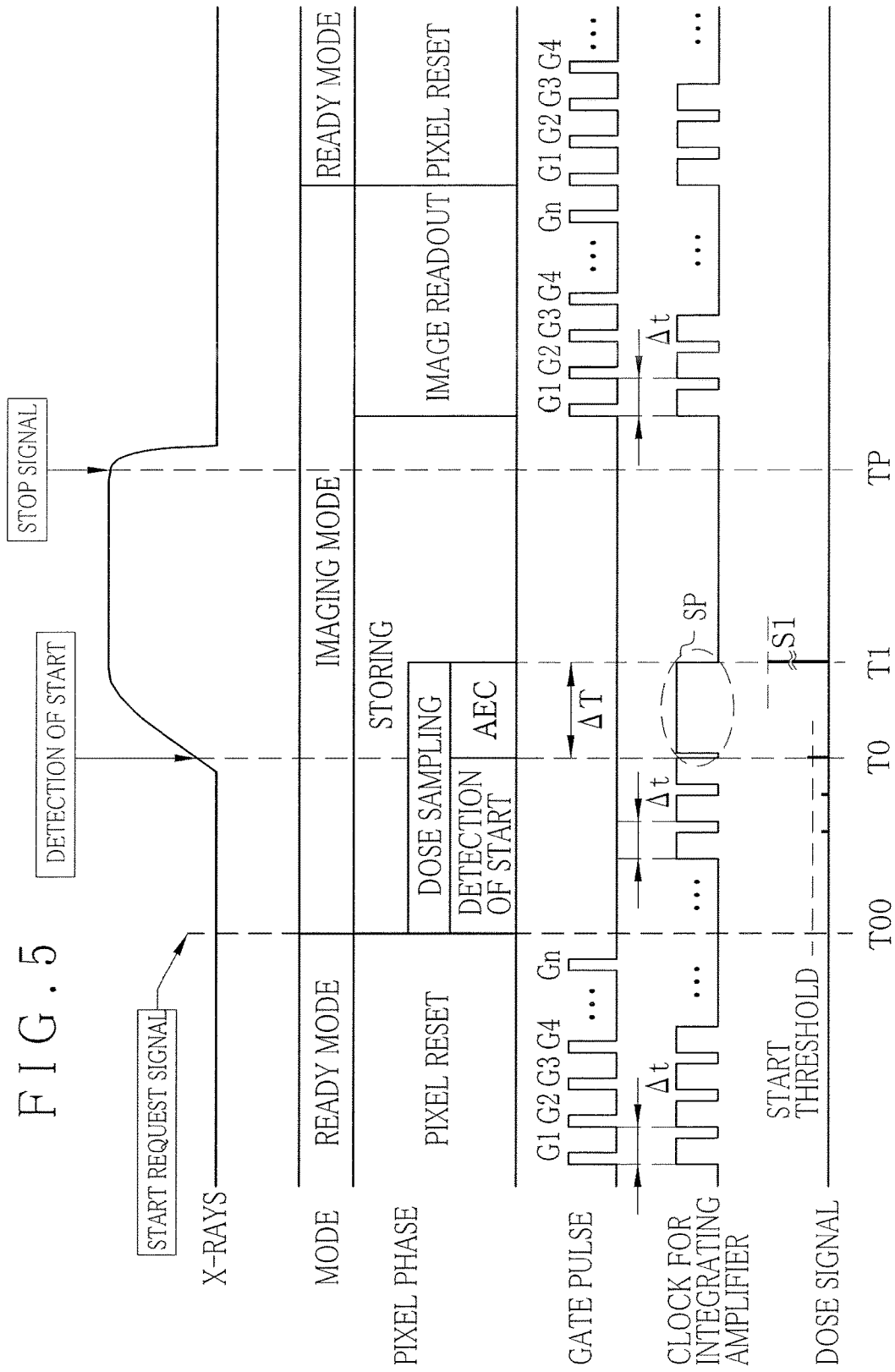
FIG. 5 is a timing chart illustrating pixel phases of a detection panel in imaging.

In FIG. 5, the controller 32 in the image readout drives the gate driver 44, the integrating amplifier 46, the CDS circuit 47, the multiplexer 48 and the A/D converter 49 at a predetermined period. The gate driver 44 sequentially generates gate pulses G1-Gn at a predetermined interval Δt (FIG. 5) to select the scan lines 42 from the first row to the nth row sequentially, so that a voltage signal of one row from the A/D converter 49 is written to the memory 51 sequentially. Upon completion of the image readout from the first row to the nth row, the memory 51 comes to store the voltage signal representing one X-ray image in correspondence with X and Y coordinates of the pixels 38. The data of the voltage signal is read out from the memory 51 to the controller 32, processed for the image processing in the controller 32, and then transmitted by the communication interface 33 to the console unit 14. Thus, the X-ray image of the object is detected. Note that the voltage signal read out in the image readout is hereinafter referred to as an image signal.

Dark current charge occurs in the semiconductor layer of the photo diode 40 irrespective of entry of X-rays. The dark current charge is stored in the normal pixels 38*a* because of application of the bias voltage. The dark current charge at the normal pixels 38*a* may become a noise component in relation to image data of the X-rays. Thus, the pixel reset is performed at a predetermined time interval to eliminate the dark current charge. The pixel reset is to sweep out the dark current charge from the normal pixels 38*a* through the signal lines 43.

The pixel reset is performed in sequential pixel reset for resetting the normal pixels 38*a* by one row. In the sequential pixel reset, the gate driver 44 generates the gate pulses G1-Gn to the scan lines 42 at a predetermined interval Δt sequentially in a manner similar to the image readout, to turn on the TFT 41 of the pixels 38 one row after another. While the TFT 41 is turned on, dark current charge flows from the normal pixels 38*a* to the capacitor 46*b* of the integrating amplifier 46 through the signal lines 43. In the pixel reset, no readout of signal charge in the multiplexer 48 is performed in a manner different from the image readout. The controller 32 outputs an amplifier reset pulse RST in synchronism with a fall of the gate pulses G1-Gn, to turn on the reset switch 46*c*. The dark current charge stored in the capacitor 46*b* is discharged to reset the integrating amplifier 46.

Also, it is possible to use the parallel pixel reset or the simultaneous pixel reset instead of the sequential pixel reset. In the parallel pixel reset, plural rows of pixels are grouped in plural groups. Pixels are reset in each of the groups by the sequential pixel reset, to sweep out dark current charge from the rows of the groups. In the simultaneous pixel reset, gate pulses are input to all of the rows to sweep out the dark current charge of all the pixels simultaneously. The use of the parallel pixel reset or the simultaneous pixel reset is effective in increasing speed of the pixel reset.

As described heretofore, the charge collected by the lower electrode of the photo diode 40 of the monitor pixels 38*b* flows out always to the first signal lines 43*a* through the short-circuit line 55. A plurality of the monitor pixels 38*b* are connected to one of the first signal lines 43*a*. The charge from at least two of the monitor pixels 38*b* is added up for flow out to the capacitor 46*b* of the integrating amplifier 46, and is stored in the capacitor 46*b*. Even during the storing of the charge in the turn-off state of the TFT 41 with the normal pixels 38*a* of the same column, the charge of the monitor pixels 38*b* can be read out by driving elements in the signal processor 45.

The controller 32 in response to the start request signal stops the operation of the pixel reset. The controller 32 causes the signal processor 45 to start sampling the dose. The dose sampling is for the purposes of detecting the start in the start detector 52 and performing the AEC in the AEC device 53, as will be described later.

The signal processor 45 performs the dose sampling of reading out the voltage signal according to the charge in the monitor pixels 38*b* at the sampling period determined by the controller 32. The charge of the monitor pixels 38*b* is changed according to a dose of incident X-rays to the imaging surface 39. The voltage signal obtained by sampling of one event represents the dose of X-rays incident on the imaging surface 39 per unit time. Let a dose signal be the voltage signal read out by the dose sampling. The signal processor 45 corresponds to a dose sampler for sampling the dose signal in the dosimetry.

In the dose sampling, the reset switch 46*c* of the integrating amplifier 46 is supplied with the reset pulse RST by the controller 32 at each event of the sampling, to reset the stored charge. In the sampling of one event, the CDS circuits 47 are sequentially selected by the multiplexer 48 in a similar manner as the readout of the image signal of one row of the image readout, to sample the dose signal of one row. The output of the monitor pixels 38*b* arranged on the imaging surface 39 flows out always to the first signal lines 43*a*. The dose signal of one row read out by the dose sampling includes a dose signal corresponding to all the monitor pixels 38*b*. The memory 51 comes to store the dose signal of the one row.

The controller 32 includes correctors or circuit elements (not shown) for image processing of various functions to an X-ray image stored in the memory 51 by image readout, for example, offset correction, sensitivity correction, defect correction and the like. The offset corrector subtracts an offset correction image from the X-ray image per unit of pixels, and eliminates offset noise due to dark current characteristic of the photo diode 40, the offset correction image being formed by image readout without using X-rays.

The sensitivity corrector is referred to also as a gain corrector, and corrects unevenness in sensitivity of the photo diode 40 in the pixels 38, unevenness in an output characteristic of the signal processor 45, or the like. The sensitivity correction is performed according to sensitivity correction data which has been produced from an image formed by subtraction of the above-described offset correction image from an image formed upon irradiation of X-rays of a predetermined dose in the absence of an object. The sensitivity correction data includes a coefficient for each of the pixels for correcting a difference from a reference value so that outputs of the pixels are regularized by multiplication of the coefficient and an X-ray image after the offset correction upon irradiation of X-rays of the predetermined dose in the absence of an object. For example, let an output of a pixel A be 1 as a reference value. Let an output of a pixel B be 0.8. A coefficient of the pixel B is 1/0.8=1.25.

The defect corrector performs linear interpolation of pixel values of defective pixels according to pixel values of normal pixels arranged thereabout by use of additional information of defective pixels initially provided at the time of factory shipment. Also, the defect corrector treats the monitor pixels 38*b* for the start detection and the AEC as defective pixels. Pixel values of the normal pixels 38*a* of a column of the first signal lines 43a with the monitor pixels 38b receive influence of an output of the monitor pixels 38b with a constant flow. The defect corrector also performs interpolation of pixel values of the monitor pixels 38b and those of the normal pixels 38a of a column of the first signal lines 43a with the monitor pixels 38b.

The offset correction image and sensitivity correction data are acquired at the time of factory shipment of the electronic cassette 13, acquired in periodic maintenance by a service engineer, or acquired at the start of daily working hours of a hospital by a physician or operator. Those data are stored in the internal memory of the controller 32, and read out for the correction. It is also possible to incorporate the correctors or circuit elements in the console unit 14, and to perform the image processing in the console unit 14.

The start detector 52 and the AEC device 53 are controlled by the controller 32. At each time of sampling the dose signal in the signal processor 45 to record the dose signal of one row in the memory 51, the start detector 52 and the AEC device 53 read out the dose signal from the memory 51.

At first, the start detector 52 and the AEC device 53 remove a dummy signal from the dose signal of one pixel row read from the memory 51. The columns of the first signal lines 43a having the monitor pixels 38b are so disposed that two or more of the second signal lines 43b without the monitor pixels 38b are disposed between those. The dose signal of one pixel row includes the dummy signal corresponding to the columns of the second signal lines 43b between dose signals of significance of the columns of the first signal lines 43a. A value of the dummy signal is as small as zero because based on leaked charge from the normal pixels 38a. Therefore, the start detector 52 and the AEC device 53 remove the dummy signal being useless as data before the detection of the start and the AEC. It is also possible to select only a dose signal according to a column of the first signal lines 43a upon reading from the memory 51, in place of eliminating the dummy signal after reading the dose signal of one pixel row from the memory 51.

In the start detection, the start detector 52 checks whether the X-ray generating apparatus 2a has started irradiation of X-rays according to the dose signal, namely, checks whether emitted X-rays have reached the detection panel 30 and are detected by the detection panel 30. The start detection is triggered upon changeover of the detection panel 30 from a ready mode of performing the pixel reset to the imaging mode of starting the storing, in response to a start request signal from the radiation source controller 11.

In the processing of detecting the start, the start detector 52 compares a representative value of the dose signal with a predetermined start threshold (turn-on threshold) of FIG. 5. The representative value is according to the dose signal from all of the monitor pixels 38b or the monitor pixels 38b present in an particular area in the detection panel 30 (for example, an open area where X-rays are passed directly without transmitting through a body part). Examples of the representative value of the dose signal are an average, maximum, mode value, total and the like of the dose signal. In case the representative value of the dose signal becomes higher than the start threshold, the start detector 52 judges that irradiation of X-rays from the X-ray source 10 has started. The start detector 52 reads out data of a present time point of the detected start from a clock (not shown), and causes storing the present time point as the start time T0. Note that it is possible to record a time point as the start time T0 for a reference in subsequent time measurement in place of the present time point.

In FIG. 5, the controller 32 sets the sampling of the dose signal at the second sampling period $\Delta t$ equal to $\Delta t$ of the interval of the gate pulses G1-Gn in the start detection of the start detector 52. Thus, the dose signal of one row is stored in the memory 51 at each time of the second sampling period $\Delta t$. The dose signal is compared with the start threshold at each time of the second sampling period $\Delta t$. The controller 32 after the start time T0 changes over the sampling of the dose signal from the second sampling period $\Delta t$ to the first sampling period $\Delta T$.

The AEC device 53 acquires a cumulative dose according to the dose signal sampled at the sampling period $\Delta T$ during irradiation of X-rays. The AEC device 53 predicts a time point of reach of the cumulative dose to a target dose according to the acquired cumulative dose. The AEC device 53 starts the dosimetry upon detection in the start detector 52 for a start of the irradiation of X-rays. The AEC device 53 acquires the cumulative dose according to the sampled dose signal at the acquisition time T1 upon the lapse of the sampling period $\Delta T$ from the start time T0. The cumulative dose is acquired according to a representative value of a dose signal from all of the monitor pixels 38b, or from one of the monitor pixels 38b disposed in a predetermined region in the detection panel 30 (for example, a region of interest of the medically highest importance in the imaging). Examples of the representative value of the dose signal are an average, maximum, mode value, total and the like of the dose signal. Estimation is performed for a time point of a predicted reach of the cumulative dose of X-rays to the target dose according to linear extrapolation.

Figures 6, 7:
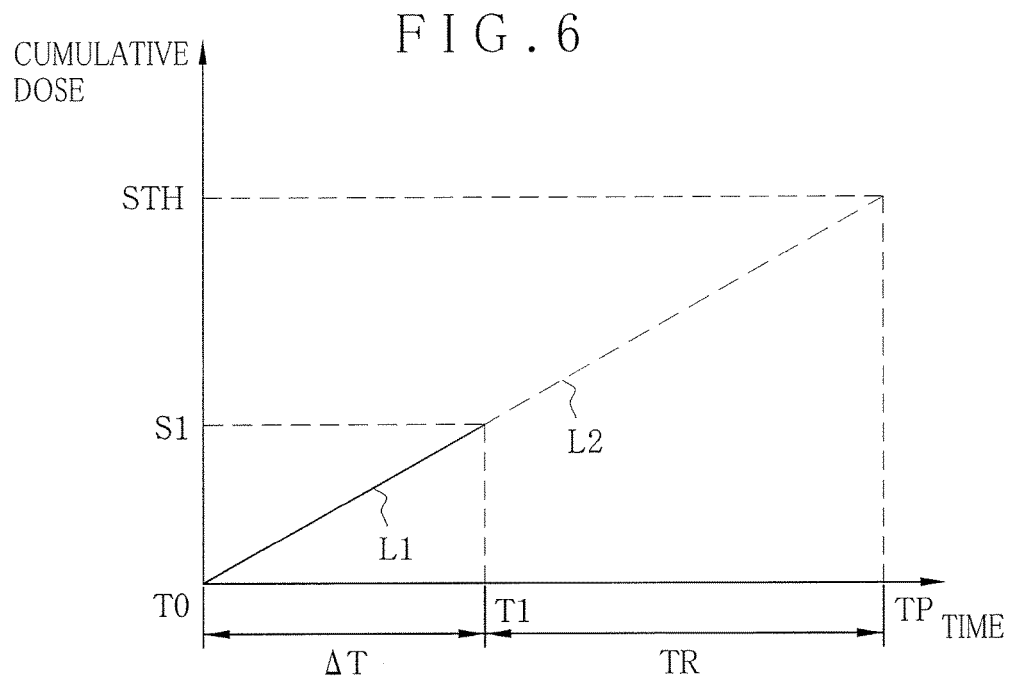
FIG. 6 is a graph illustrating a method of estimating a predicted time point of an increase in the dose.
FIG. 7 is a table illustrating an imaging condition.

As illustrated in FIG. 6, an interpolation line L1 is plotted by use of the start time T0 as an origin and the metered dose S1 as cumulative dose acquired at the acquisition time T1, to express a change of the cumulative dose with time. As the start time T0 is time of detected start of irradiation of X-rays, the cumulative dose at the start time T0 can be estimated as small as zero. Also, the AEC device 53 plots an extrapolation line L2 by extending the interpolation line L1 after the acquisition time T1. A predicted time point TP is estimated as time where the extrapolation line L2 reaches a stop threshold STH (turn-off threshold) as target dose. The AEC device 53 also determines remaining time TR as a difference between the predicted time point TP and the acquisition time T1.

The start time T0 is detected time of having starting irradiation in comparison of the dose signal with the start threshold in the start detector 52, and is slightly later than an actual start time of irradiation of X-rays. Thus, the cumulative dose at the start time T0 is not exactly equal to zero. Note that the estimation can be performed in a strictly exact manner. Metered dose S0 as a cumulative dose at the start time T0 can be acquired according to the dose signal for use in the comparison with the start threshold. In the structure, the AEC device 53 uses the metered dose S0 as cumulative dose at the start time T0, and estimates a predicted time point TP according to the metered dose S0 and the metered dose S1 at the time T1.

The sampling period $\Delta T$ (first sampling period) is time from the start time T0 to the acquisition time T1, and is a storing period SP of storing charge output by the monitor pixels 38b in the integrating amplifier 46. The AEC device 53 can acquire the metered dose S1 at the acquisition time T1 according to the dose signal output by sampling of one event in the signal processor 45 with the sampling period $\Delta T$ in the AEC. Should the sampling period $\Delta T$ be too short, reliability in the estimation in the AEC device 53 will be low. This is because the S/N ratio of the dose signal decreases according to shortness of the storing period SP of the charge. Should the sampling period ΔT be too long, the cumulative dose may reach the target dose in the sampling period. Consequently, the sampling period ΔT is determined suitably in consideration of the reliability of the prediction and the irradiation time.

The AEC device 53 has a timer in which remaining time TR according to the estimation is set. In case the timer performs measurement to detect that the remaining time TR has become zero, the AEC device 53 causes the controller 32 to output a stop signal to the communication interface 33.

An interface device 54 (I/F) or irradiation signal interface device is incorporated in the communication interface 33 in FIG. 4. The sensor interface 25 of the radiation source controller 11 becomes connected to the interface device 54 in a wired manner or wirelessly. The interface device 54 receives a start request signal, transmits an enable signal in response to the start request signal, and transmits a stop signal from the AEC device 53. It is also possible to transmit information of the predicted time point TP to the radiation source controller 11 as an AEC signal instead of the stop signal. Furthermore, information of the remaining time TR can be transmitted to the radiation source controller 11 as an AEC signal. The radiation source controller 11 upon receiving the predicted time point TP and the remaining time TR counts down the remaining time TR with a timer or by estimating the predicted time point TP. The radiation source controller 11 stops irradiation of X-rays upon reach to the predicted time point TP or upon decrease of the remaining time TR to zero.

In FIG. 7, a data table 60 of an imaging condition is stored in the storage medium 14c of the console unit 14. Data of the imaging condition include information of a body part, sex, age and other personal data of a body, and the like (only the body part being illustrated in FIG. 7), also an irradiation condition of X-rays such as the tube voltage, tube current and irradiation time, and stop threshold for use in the AEC of the radiation switch 12, sampling period ΔT of the AEC, and the like. Note that a start threshold of the irradiation is constant irrespective of the body part.

The data table 60 includes recorded data of a relationship between body parts, such as chest and abdomen, and irradiation conditions. The user input interface 14a is manipulated to designate one of the body parts, to read out one of the irradiation conditions related to the body part from the storage medium 14c. The display 14b displays the irradiation condition in a display area. Values of the irradiation condition read out from the data table 60 are finely adjustable according to personal information of the body, such as sex, age, body thickness and the like. A physician or operator checks the imaging request in the display 14b, and inputs a suitable imaging condition with the user input interface 14a. Information of the imaging condition is transmitted by the console unit 14 to the electronic cassette 13. He or she reviews the irradiation condition set in the console unit 14, and manually sets the irradiation condition in the radiation source controller 11.

In the use of the AEC function, the irradiation time set in the console unit 14 does not mean a stop of irradiation of X-rays with the value of the irradiation time. The irradiation time is simply a recommended value according to a local thickness of a body part. In the data table 60 of the embodiment, the tube current and irradiation time are recorded discretely from one another. However, a current/time product (mAs value) can be recorded instead, because the product of the tube current and irradiation time determines a total of the irradiation dose of X-rays.

Figure 8:
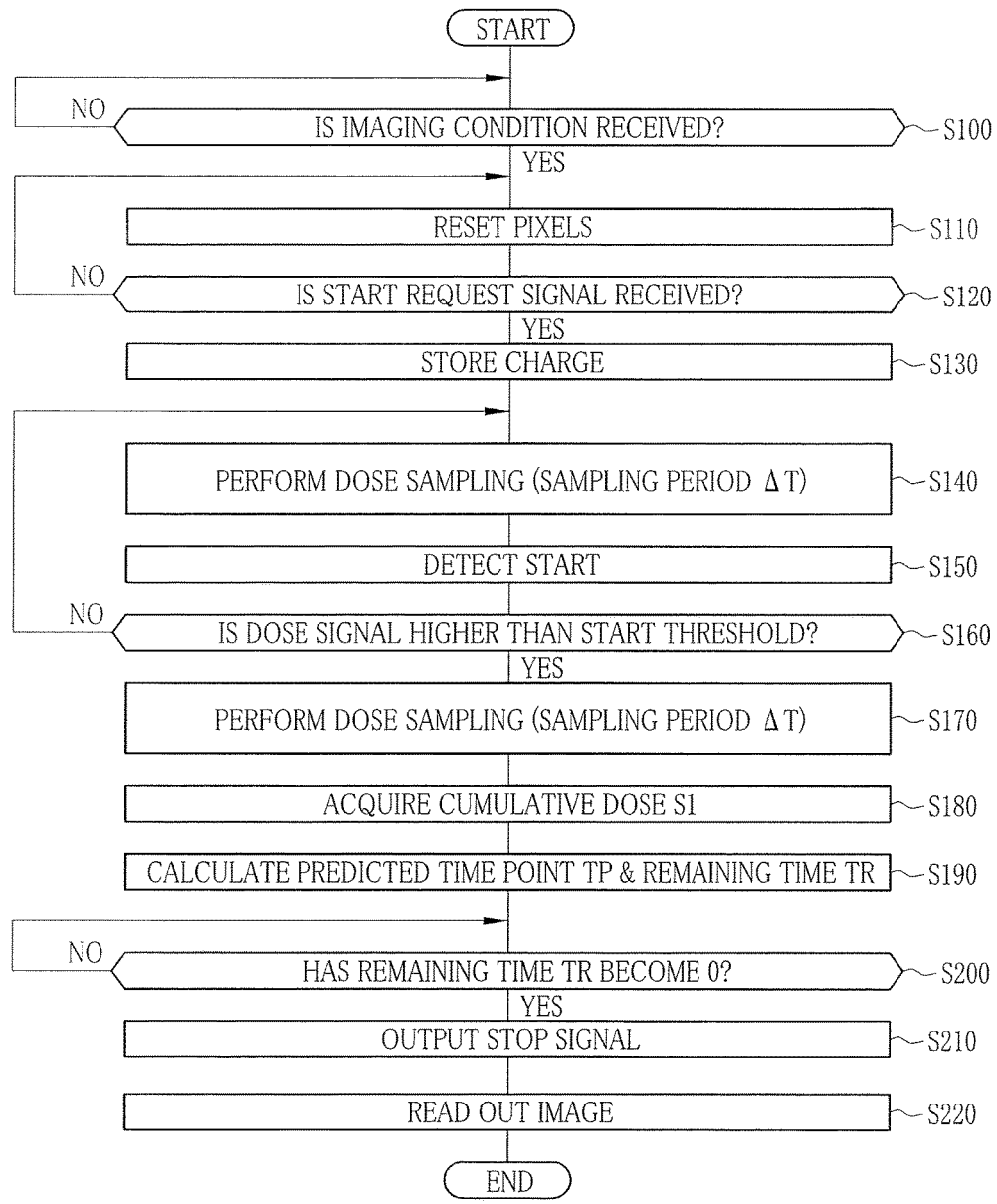
FIG. 8 is a flow chart illustrating pixel phases of the electronic cassette.

The operation of the above construction is described now by referring to FIGS. 5 and 8. At first, a body of a patient is positioned erectly in front of the standing orientation imaging station 15 or horizontally on the horizontal orientation imaging station 16 for X-ray imaging in the X-ray imaging system 2. The electronic cassette 13 set in one of the imaging stations 15 and 16 for use is adjusted for the height, horizontal position and the like, to place a body part in the body at the electronic cassette 13. Also, a height, horizontal position and irradiation area of the X-ray source 10 are adjusted according to the position of the electronic cassette 13 and a size of the body part. Then one of the two electronic cassettes 13 is selected by the console unit 14. An imaging condition is set in the console unit 14. Also, an irradiation condition of X-rays in the same manner as the console unit 14 is set in the radiation source controller 11. The imaging condition set in the console unit 14 is transmitted to the electronic cassette 13.

After setting the imaging condition in the console unit 14 and setting the irradiation condition in the radiation source controller 11, a physician or operator depresses the radiation switch 12. In response, a warmup start signal is input to the radiation source controller 11 to start warming up the X-ray source 10. The radiation source controller 11 also sends a start request signal to the electronic cassette 13 for start.

The electronic cassette 13 in a sleep mode in which only the communication interface 33 is active is ready to receive the imaging condition from the console unit 14. In FIG. 8, the detection panel 30, upon receiving the imaging condition from the console unit 14 (yes in the step S100), starts the pixel reset, and changes over from the sleep mode to the ready mode in the step S110. In the pixel reset, the gate driver 44 outputs gate pulses. Reset is cyclically repeated at a predetermined period, in which unwanted charge is read out from the normal pixels 38a of one row to the signal lines 43, and abandoned in the integrating amplifier 46. In the electronic cassette 13, the interface device 54 waits for the start request signal from the sensor interface 25.

The radiation switch 12 is depressed at a first step to transmit a start request signal through the sensor interface 25. In case the interface device 54 receives the start request signal (yes in the step S120 at the reception time T00), then the detection panel 30 performs the pixel reset up to the nth pixel row, and starts the storing, to change over from the ready mode to the imaging mode (step S130). At the same time, the interface device 54 transmits an enable signal. In the pixel phase of the storing, no gate pulse is generated by the gate driver 44, so that the normal pixels 38a store signal charge according to a dose of applied X-rays.

At the same time as the start of the storing, the dose sampling at the sampling period Δt is started in the step S140 for the start detection. The charge in the monitor pixels 38b (detection pixels) flows out to the signal lines 43 and is stored in the integrating amplifier 46, as the source and drain of the TFT 41 are short-circuited. In the dose sampling, the dose signal is sampled according to the charge stored in the integrating amplifier 46 from the monitor pixels 38b. The charge stored in the integrating amplifier 46 is reset at each time of the sampling. The CDS circuits 47 are sequentially selected by the multiplexer 48 in one event of sampling, to write the dose signal of one row to the memory 51.

After the radiation switch 12 is depressed at the first step, the operator depresses the radiation switch 12 at a second step upon estimating lapse of the time of the warmup. In response to the depression of the radiation switch 12, the radiation source controller 11 is supplied with a turn-on signal, to start irradiation of X-rays from the X-ray source 10.

At the same time as the changeover to the imaging mode, the start detector 52 triggers the start detection according to the dose signal in the step S150. The dose signal of one row stored in the memory 51 is read out by the start detector 52 at each time of sampling. The start detector 52 calculates a representative value of the dose signal at each time of the sampling, and compares the representative value with the predetermined start threshold. There is a time lag from the reception time T00 of the start request signal to actual irradiation of X-rays. The dose signal in the time lag is a very low value based on dark current charge generated in the monitor pixels 38*b*. In case X-rays are emitted by the X-ray source 10 and reach the detection panel 30, the monitor pixels 38*b* perform monitoring to increase an amount of the charge. A dose signal of this time point increases and becomes higher than the start threshold. Finally, the start detector 52 detects the start of the irradiation of X-rays (yes in the step S160 at the start time T0).

In case the start detector 52 judges that irradiation of X-rays has been started, then the sampling period of the dose signal is changed from $\Delta t$ to $\Delta T$ by the controller 32. The dose sampling is continued in the step S170. In FIG. 5, a row of the clock of the integrating amplifier is indicated with the storing period SP of the broken line. Assuming that the start detector 52 judges that irradiation of X-rays has been started, then the controller 32 resets the integrating amplifier 46, and then causes the integrating amplifier 46 to start storing the charge from the monitor pixels 38*b* through the signal lines 43. The controller 32 samples the dose signal according to the stored charge of the integrating amplifier 46 at the acquisition time T1 upon the lapse of the predetermined sampling period $\Delta T$ from the start time T0. The dose signal is stored to the memory 51 in the step S180. After outputting the dose signal, the detection panel 30 completes the dose sampling. However, the storing is continued.

The dose signal sampled at the acquisition time T1 is a signal representing the cumulative dose S1 from the start time T0 to the acquisition time T1. The AEC device 53 acquires the cumulative dose S1 according to the sampled dose signal. The AEC device 53 acquires the predicted time point TP at the reach of the extrapolation line L2 to the stop threshold STH (turn-off threshold), the extrapolation line L2 being an extension of an interpolation line L1 plotted from the origin at the start time T0 to the cumulative dose S1 at the acquisition time T1. Then the AEC device 53 calculates the remaining time TR by subtracting the acquisition time T1 from the predicted time point TP in the step S190.

The remaining time TR is set in the timer of the AEC device 53. In case the remaining time TR becomes zero (yes in the step S200 at the time TP), the AEC device 53 outputs a stop signal in the step S210. The interface device 54 transmits a stop signal to the sensor interface 25. The radiation source controller 11 in response to the stop signal stops the X-ray source 10 from emitting X-rays. Assuming that no stop signal is received by the radiation source controller 11, the X-ray source 10 is stopped from irradiation upon lapse of the irradiation time predetermined in the radiation source controller 11.

Upon the lapse of a predetermined time after transmitting the stop signal, the controller 32 changes over the detection panel 30 from the storing to the image readout in the step S220. In the image readout, the gate driver 44 generates a gate pulse. The signal charge in the normal pixels 38*a* for one row is read out to the signal lines 43. The image signal of one row according to the signal charge is output from the integrating amplifier 46, converted digitally by the A/D converter, and written to the memory 51. Those steps are cyclically repeated. Thus, the memory 51 comes to store the image signal of one X-ray image. The detection panel 30 returns to the ready mode for pixel reset. Note that the dose of X-rays after outputting the stop signal does not become zero immediately but decreases gradually, in the irradiation profile of changes with time of the dose of the X-rays per unit time. In the present embodiment, the storing is changed over to the image readout upon the lapse of the predetermined time after transmission of the stop signal, for the purpose of absorbing a component of the gradual decrease.

The X-ray image output to the memory 51 by the image readout is processed in various functions of image processing by image processing circuits of various types, and transmitted to the console unit 14 through the communication interface 33 in a wired manner or wirelessly, so that the display 14*b* displays the X-ray image for diagnosis. Thus, one event of the X-ray imaging is completed.

As described heretofore, the start time T0 is detected by detecting the start of irradiation of X-rays in the start detector 52. The AEC device 53 acquires the metered dose S1 as cumulative dose from the start time T0 to the acquisition time T1. The predicted time point TP is estimated for reach of the cumulative dose to the stop threshold STH according to the metered dose S1. Thus, the estimation of the predicted time point TP can be performed rapidly.

It is necessary to find cumulative doses of at least two time points in order to predict a time point of reach of the cumulative dose to the stop threshold STH according to the linear extrapolation or the like. In the prior art (JP-A 2010-075556), the start time T0 cannot be recognized, so that the cumulative dose must be measured at two time points after the start time T0. In contrast with this, the start time T0 is detected by the start detector 52 in a condition with the cumulative dose being as small as zero. Thus, acquiring the cumulative dose (metered dose S1) at one time point at or after the start time T0 is effective in recognizing a change of the cumulative dose with time from the origin of the start time T0. The predicted time point TP can be estimated for a reach of the cumulative dose to the stop threshold STH. In conclusion, estimation of the predicted time point TP can be performed rapidly, because the cumulative dose after the start time T0 can be performed only in one event.

It is possible in the invention to estimate the predicted time point TP by acquiring the cumulative dose of at most one event of dosimetry. Enough time can be ensured for obtaining a dose signal with high reliability for use in the dosimetry in comparison with the prior art (JP-A 2010-075556) in which dosimetry of two events is required during the irradiation. Also, the feature of the invention is effective in imaging of a low dose with a short irradiation time, because the predicted time point TP can be estimated by acquiring the cumulative dose of at most one event of dosimetry.

Also, a time lag from reception of a sync signal such as a start request signal for irradiation until actual irradiation of X-rays is changeable with an imaging condition or the like. In the prior art (JP-A 2010-075556), it is necessary to determine acquisition time of acquiring a cumulative dose at a first event by considering the time lag. However, it is unnecessary in the invention to consider the time lag, because the start time T0 is detected. Thus, estimation of a predicted time point can be performed at a short time because the acquisition time can be set nearer to the start time T0 than in the prior art.

Should long time be required for estimating the predicted time point TP, the cumulative dose may reach the target dose before terminating the estimation so that longer time may pass than is enough for irradiation of X-rays. The body or object is likely to receive unwanted irradiation. However, possibility of such difficulty can be lower in the invention than according to the prior art.

At the start time T0, storing charge from the monitor pixels 38b is started after resetting the integrating amplifier 46. Thus, it is possible at the acquisition time T1 to acquire a dose signal without a component of the dark current charge until the start time T0. Reliability of the predicted time point TP can be increased as the metered dose S1 is acquired according to the dose signal.

In the embodiment, the sampling period $\Delta T$ is from the start time T0 to the acquisition time T1, to acquire the dose signal of the metered dose S1 only at one event of sampling. This is effective in acquiring the dose signal of a high S/N ratio with the long sampling period in comparison with dosimetry of the metered dose S1 by adding up the dose signals of the sampling of plural events. Also, reliability of the predicted time point TP can be high.

In the present embodiment, the dose sampler for the sampling samples the dose signal at a sampling period $\Delta t$ shorter than the sampling period $\Delta T$ until the start detector 52 detects a start of the irradiation, and changes over to the sampling period $\Delta T$ after the start time T0 of detecting the start. Thus, the detection of the start can be performed rapidly, as the dose signal is sampled at a short interval for the detection of the start. In contrast, the sampling period for the AEC is set longer to obtain a dose signal with a high S/N ratio. Reliability of the predicted time point TP can be ensured.

In the embodiment, the monitor pixels 38b for dosimetry are the radiation monitoring device used both for detecting the start of the irradiation and for the AEC. Thus, a manufacturing cost can be lower than an alternative structure in which radiation monitoring devices are disposed discretely for detecting the start of the irradiation and for the AEC.

As the monitor pixels 38b are included in the pixels 38, the manufacturing cost can be smaller than a structure in which a radiation monitoring device is added to the detection panel 30. Furthermore, the signal processor 45 for the readout can be used also for dose sampling with the monitor pixels 38b included in the pixels 38. The manufacturing cost can be reduced.

Figure 9:
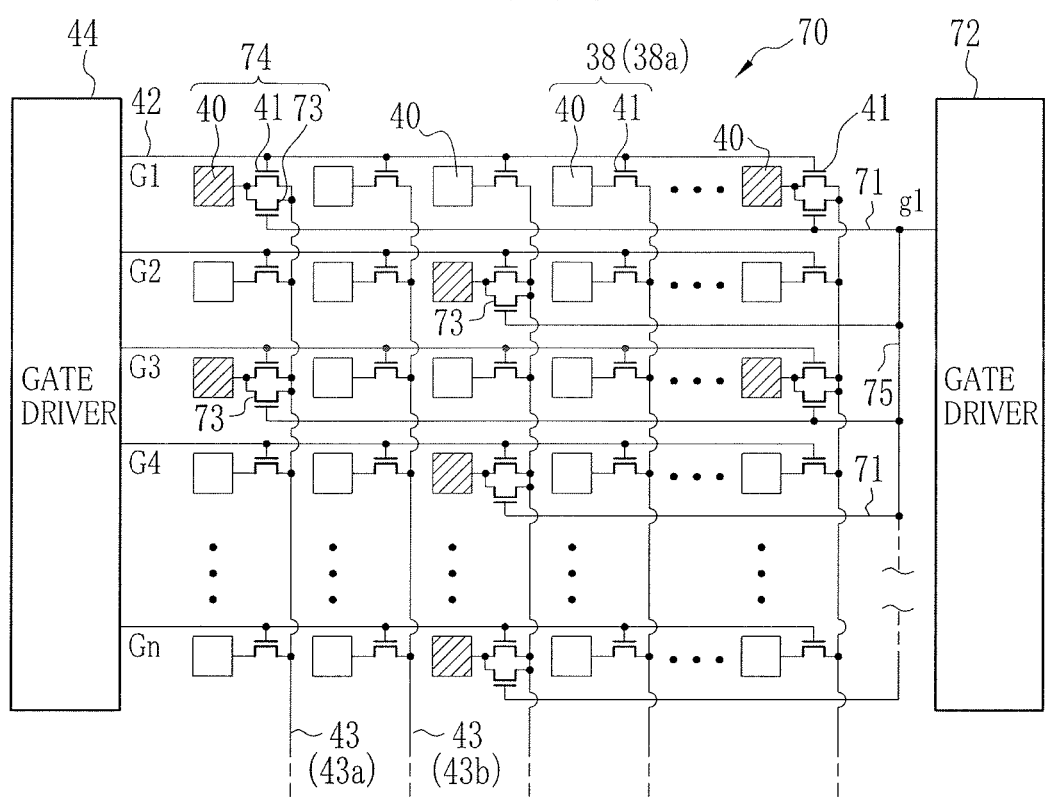
FIG. 9 is a block diagram schematically illustrating another preferred detection panel with monitor pixels of a variant.

In the above embodiment, the source and drain in the TFT 41 are short-circuited in the monitor pixels 38b. However, a monitor pixel may not have the TFT 41 and can have the photo diode 40 directly connected to the signal lines 43. In FIG. 9, another preferred detection panel 70 has pixels 74 by way of monitor pixels. There are scan lines 71 and a gate driver 72 discrete from the scan lines 42 and the gate driver 44 for driving the TFT 41. TFTs 73 are driven by the scan lines 71 and the gate driver 72. The pixels 74 have the TFTs 73 in addition to the TFTs 41.

The scan lines 71 are disposed in parallel with the scan lines 42 in rows having the pixels 74. The scan lines 71 are connected to one bus line 75 between the scan lines 71 and the gate driver 72. The bus line 75 is connected to the gate driver 72. In case a gate pulse g1 is output to the bus line 75 by the gate driver 72, all of the TFTs 73 are turned on. Charge generated by the pixels 74 comes to flow to the capacitor 46b in the integrating amplifier 46 through the first signal lines 43a. The gate driver 72 is controllable discretely from the gate driver 44, and can read out the charge generated by the pixels 74 even while the TFT 41 is turned off and the normal pixels 38a operate for the storing. Note that only the TFTs 73 can be provided in the pixels 74 without the TFT 41.

Figure 10:
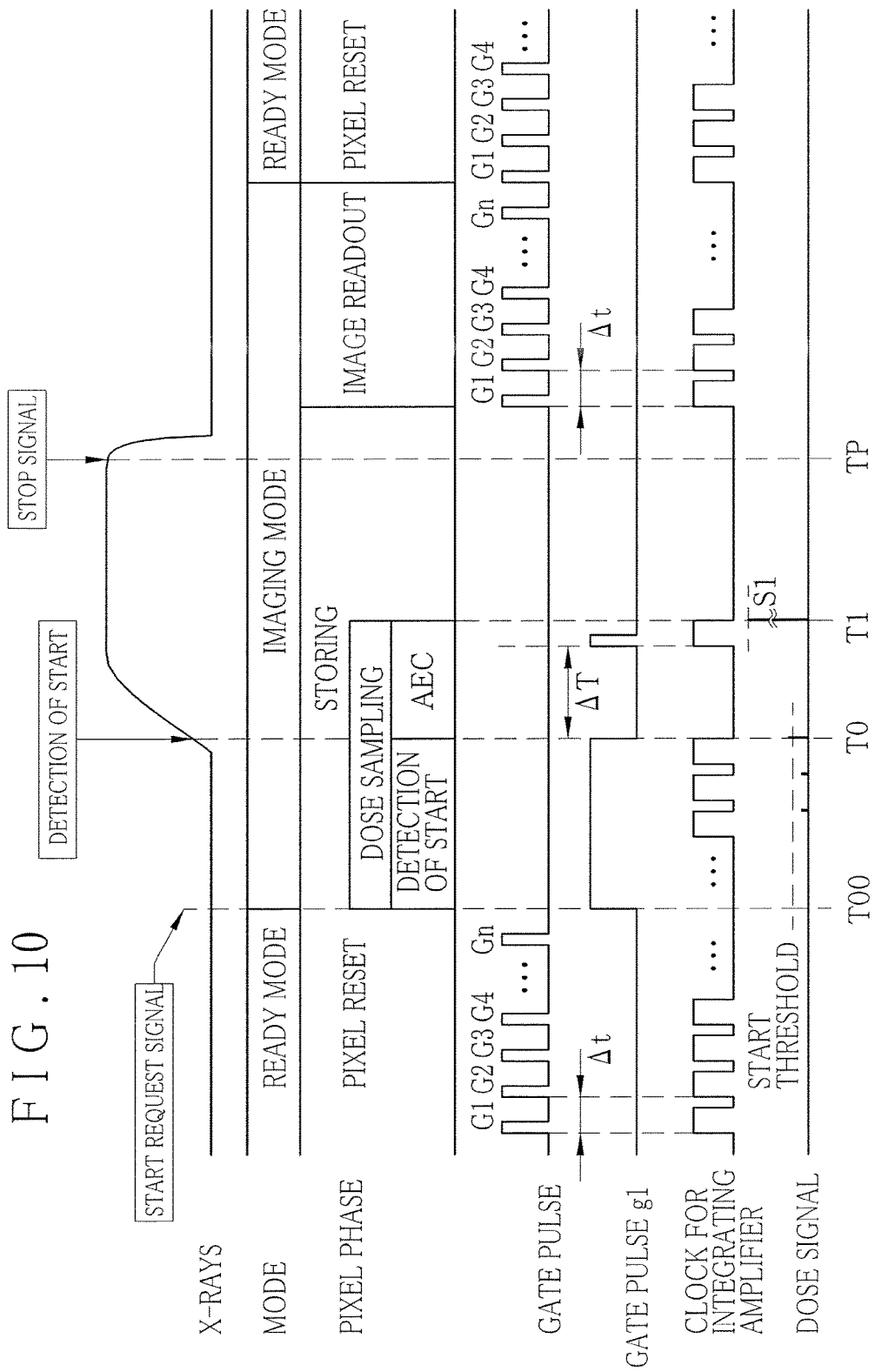
FIG. 10 is a timing chart illustrating pixel phases of the detection panel in imaging.

For the start detection in FIG. 10, the gate driver 72 continuously outputs the gate pulse g1 to the bus line 75, to turn on the TFTs 73. Charge generated by the pixels 74 is caused to flow through the first signal lines 43a to the capacitor 46b of the integrating amplifier 46. In a manner similar to the above embodiment, the dose signal is sampled according to the charge generated by the pixels 74 at a sampling period equal to the interval $\Delta t$ of the gate pulses G1-Gn.

In case the start detector 52 detects a start of irradiation of X-rays (start time T0) with a higher level of the dose signal than the start threshold, then an output of the gate pulse g1 is stopped to set the pixels 74 for the storing. This state is kept until the acquisition time T1 upon lapse of the sampling period $\Delta T$. At the acquisition time T1, the gate pulse g1 is generated again, so that charge generated by the pixels 74 during the sampling period $\Delta T$ is caused to flow into the capacitor 46b of the integrating amplifier 46. A dose signal according to this is output to the AEC device 53. For the remaining portions of the processing, the above embodiment is repeated.

Figure 11:
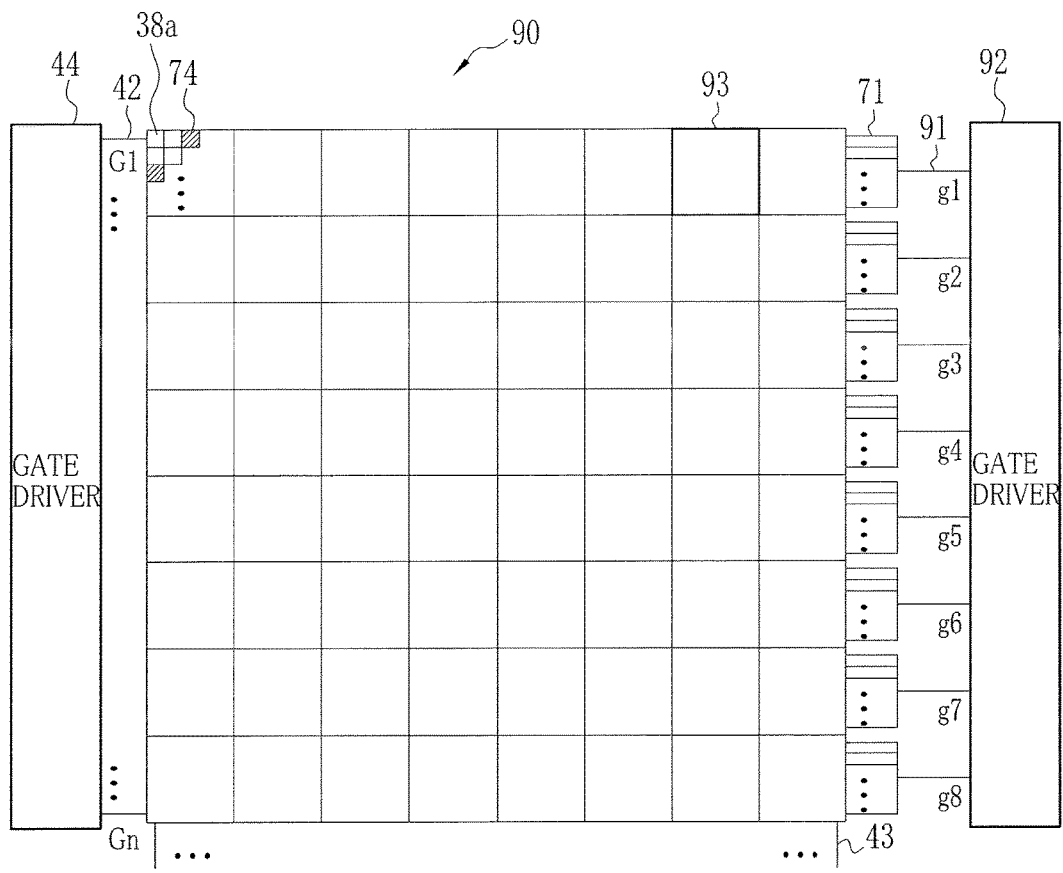
FIG. 11 is an explanatory view illustrating another preferred detection panel of which pixels are grouped.

In the embodiment of FIG. 9, the bus line 75 as a single line is associated with all the scan lines 71 for readout of charge from the pixels 74 only with the gate pulse g1. However, it is possible to supply each of the scan lines 71 with a gate pulse without the bus line 75 in a manner similar to the gate driver 44. Furthermore, FIG. 11 illustrates another preferred detection panel 90. The scan lines 71 are grouped by use of bus lines 91 in forms of array groups having plural adjacent scan lines. A gate driver 92 outputs a gate pulse to each of the bus lines 91 of one of the array groups. In the embodiment, the gate pulses g1-g8 are supplied to the bus lines 91 of eight array groups arranged in the imaging surface 39.

According to the construction of FIG. 11, it is possible to change an area of sampling a dose signal in compliance with purposes, for example, to output only a gate pulse g1 for detecting the start to sample the dose signal selectively from an uppermost array group, to output only gate pulses g4 and g5 for the AEC to sample the dose signal selectively from fourth and fifth array groups at the center, and the like.

Figure 12:
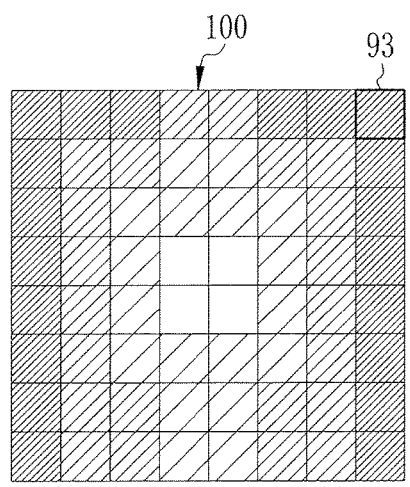
FIG. 12 is an explanatory view illustrating a dose distribution.

Furthermore, pre-irradiation can be performed to apply X-rays of a low dose to a body before the X-ray imaging of the purpose, so as to determine an array group for which a dose signal is sampled at the time of the AEC according to a result of the pre-irradiation. To this end, gate pulses g1-g8 are generated sequentially after the pre-irradiation, to read out the charge in the pixels 74 for sampling the dose signal. There are 8×8 blocks 93 equally arranged on the imaging surface 39. An average of the dose signal is obtained for each of the blocks 93. A dose distribution 100 or dose map of FIG. 12 is produced from the average.

The dose distribution 100 is a map image of values of X-ray doses of the detection panel 90 according to the blocks 93. Among the blocks 93, open areas of direct transmission of X-rays without passing a body part are indicated with dense hatching to represent a high value. Large thickness areas of transmission of X-rays through the body part with considerable thickness is indicated with blank areas to represent a low value. Small thickness areas of transmission of X-rays through the body part with small thickness is indicated with light hatching to represent a medium low value. For the AEC in the X-ray imaging of a body, the dose distribution 100 is referred to for sampling the dose signal selectively from part of the array groups which the blocks 93 of the blank area belong to.

In the above embodiments, the cumulative dose (metered dose S1) is acquired only at one event after the start time T0, to estimate the predicted time point TP. However, the cumulative dose can be acquired in two or more events for increasing reliability of the estimation. The acquisition time T1 of the first event can be set nearer to the start time T0 than according to the prior art (JP-A 2010-075556), because the start time T0 is detected. The estimation of the predicted time point can be performed rapidly in a short time. Note that the number of the events of the dosimetry of the cumulative dose is preferably two or three. This is because the required time for the dosimetry may be longer so as to reduce the effect of the feature of the invention in which the predicted time point TP is rapidly estimated in a short time.

Also, it is possible to perform the dosimetry in one event normally, but to perform the dosimetry in a second event only assuming that the metered dose S1 of the first event at the acquisition time T1 is equal to or less than a predetermined lower limit. The lower limit is such a value that reliability of the estimation of a predicted time point TP will becomes more than a tolerable range assuming that the metered dose is equal to or less than the lower limit. Let $\Delta T$ be a sampling period. The dosimetry of the second event is performed at acquisition time T2 upon a lapse of the sampling period $\Delta T$ from the acquisition time T1. The dosimetry of the second event being required, a dose signal is sampled at the acquisition time T1, before the storing is continued without resetting the amplifier 50. Note that it is possible in the estimation to use dosimetry results of the first and second events, or to use a dosimetry result of only the second event.

To use the first and second dosimetry results, the predicted time point TP is estimated according to three values including the metered doses S1 and S2 of the acquisition time T1 and T2 and the cumulative dose at the start time T0. To use only the second dosimetry result, the predicted time point TP is estimated according to two values other than the metered dose S1, which is abandoned as an error in the monitoring. Therefore, estimation of the predicted time point TP can be performed rapidly in a short period assuming that the first metered dose S1 is higher than a lower limit. Also, reliability in predicting the predicted time point TP can be increased assuming that the first metered dose S1 is equal to or lower than the lower limit.

In the above embodiments, the monitor pixels 38b for dosimetry are discrete from the normal pixels 38a for imaging. However, the normal pixels 38a can be utilized for dosimetry without disposing the monitor pixels 38b in the detection panel. Even while the TFTs are turned off, there occurs a leak charge of a fine amount from the normal pixels 38a to the signal line. The amount of the leak charge increases according to an increase in the amount of the stored charge of the normal pixels 38a (corresponding to a dose of incident X-rays). Thus, a dose signal can be sampled by storing the leak charge in the signal line by use of an integrating amplifier. The sampled dose signal can be used for detecting the start and the AEC. Furthermore, a radiation monitoring device specialized for detecting the start and the AEC can be disposed between the pixels 38 in the detection panel in a manner distinct from the pixels 38.

Also, the dose signal can be sampled according to a current flowing through a bias line in connection with a particular pixel, by utilizing a flow of a current according to charge generated by the pixel through the bias line for supplying pixels with bias voltage. In this structure, a radiation monitoring device is constituted by a current detector for detecting the current in the bias line. Also, a dose sampler is added for integrating a current detected by a current detector, to sample the dose signal. Furthermore, it is possible in the invention to use a an ionization chamber (ion chamber) well-known in the art in addition to the detection panel, by way of a radiation monitoring device for dosimetry.

In the above embodiments, the stop signal and the like are transmitted between the source control unit and the electronic cassette. However, the stop signal and the like can be transmitted through a console unit between the source control unit and the electronic cassette.

In the above embodiment, the electronic cassette 13 is discrete from the console unit 14. However, a component of the console unit 14 may be incorporated in the electronic cassette 13. Also, a composite apparatus can be used and can include components of the radiation source controller 11 and the console unit 14. In the above embodiment, the electronic cassette is portable. However, an X-ray imaging apparatus of the invention can be an installed type for an imaging stand without portability.

In the above embodiment, the detection panel is the TFT type. However, a detection panel of the invention can be a CMOS type (complementary metal oxide semiconductor type). Non-destructive readout is possible in the CMOS type, in which signal charge is kept stored in the pixels and read out as signal voltage through amplifiers at the pixels without flowing out of the signal charge in the pixels to the signal lines. Even during the storing, it is possible to select desired pixels and to sample their dose signals from the pixels. In the CMOS type, all of a circuit group including an amplifier for reading a signal voltage is operated as a dose sampler for dosimetry. Also, all pixels of the CMOS type can be functioned by way of a radiation monitoring device.

In the embodiments, the radiation is X-rays. However, radiation for use in a radiographic imaging system of the invention can be gamma rays or the like.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An x-ray imaging apparatus comprising:
 a detection panel, having plural pixels, for detecting a dose of x-ray radiation received by an object exposed to x-ray radiation from an x-ray radiation generating apparatus; said detection panel storing signal charge according to the detected x-ray radiation and outputting an image signal from the detected x-ray radiation, for generating an image of said object;
 an x-ray radiation monitoring device for monitoring said x-ray radiation incident upon said detection panel;
 a dose sampler for sampling a dose signal of said dose of said x-ray radiation per unit time according to an output of said x-ray radiation monitoring device;
 a start detector for detecting a start of irradiation of said x-ray radiation from said x-ray radiation generating apparatus according to comparison of said dose signal with a predetermined start threshold;

an autoexposure control device for acquiring a cumulative dose of said x-ray radiation according to said dose signal from a start time of the start of irradiation detected by said start detector until acquisition time at which the dose sampler samples the dose signal, for estimating a predicted time point of reach of said cumulative dose to a stop threshold according to said start time and said acquisition time, and for stopping said x-ray irradiation of said radiation from said x-ray radiation generating apparatus at said predicted time point.

2. An x-ray imaging apparatus as defined in claim 1, wherein said autoexposure control device obtains a correlation of said cumulative dose to elapsed time according to said cumulative dose at said start time and said acquisition time, and acquires said predicted time point corresponding to said stop threshold by performing extrapolation according to said correlation.

3. An x-ray imaging apparatus as defined in claim 2, wherein said dose sampler outputs said dose signal by one sampling from said start time.

4. An x-ray imaging apparatus as defined in claim 3, wherein said dose sampler includes an integrating amplifier for storing charge output by said x-ray radiation monitoring device, and outputting said dose signal according to said stored charge.

5. An x-ray imaging apparatus as defined in claim 3, wherein a first sampling period of sampling said dose signal from said start time is set equal to a length from said start time to said acquisition time by said dose sampler.

6. An x-ray imaging apparatus as defined in claim 5, wherein said dose sampler samples said dose signal at a second sampling period shorter than said first sampling period before said start time, and switches sampling over to said first sampling period when said start time begins.

7. An x-ray imaging apparatus as defined in claim 1, wherein said autoexposure control device outputs a control signal for stopping said irradiation by said x-ray radiation generating apparatus at said predicted time point.

8. An x-ray imaging apparatus as defined in claim 7, wherein said control signal is a stop signal, output at said predicted time point, for stopping said irradiation by said x-ray radiation generating apparatus.

9. An x-ray imaging apparatus as defined in claim 7, wherein said control signal is a signal of said predicted time point or a signal of remaining time until said predicted time point.

10. An x-ray imaging apparatus as defined in claim 1, wherein in a case where said cumulative dose after said start time is equal to or lower than a lower limit, said autoexposure control device acquires a second cumulative dose upon a lapse of a sampling period from the acquisition time, to estimate said predicted time point.

11. An x-ray imaging apparatus as defined in claim 5, wherein said object is a human or animal subject having a body, and wherein said first sampling period is adjusted based on a selected part or region of said body to be imaged.

12. An x-ray imaging apparatus as defined in claim 1, wherein said x-ray radiation monitoring device is constituted by at least part of said pixels.

13. An x-ray imaging apparatus as defined in claim 12, wherein said pixels include:
normal pixels for receiving said x-ray radiation and outputting said signal charge to a signal line;
monitor pixels for constituting said x-ray radiation monitoring device and outputting charge discretely from said normal pixels.

14. An x-ray imaging apparatus as defined in claim 12, further comprising a signal processor for reading out said signal charge from said pixels, the signal processor constituting said dose sampler.

15. An x-ray imaging apparatus as defined in claim 1, wherein said detection panel is a portable electronic cassette.

16. An x-ray imaging method of detecting an x-ray radiation image of an object by use of a detection panel having plural pixels, the detection panel detecting a dose of x-ray radiation received by said object exposed to x-ray radiation from an x-ray radiation generating apparatus, storing signal charge according to the detected x-ray radiation, and outputting an image signal from the detected x-ray radiation, for generating the x-ray radiation image of said object, the method comprising:
monitoring said x-ray radiation incident upon said detection panel;
sampling a dose signal of said dose of said x-ray radiation per unit time according to a result of monitoring said x-ray radiation;
detecting a start of irradiation of said x-ray radiation from said x-ray radiation generating apparatus according to comparison of said dose signal with a predetermined start threshold;
acquiring cumulative dose of said x-ray radiation according to said dose signal from a start time of said detected start of said irradiation until acquisition time at which the dose sampler samples the dose signal;
estimating a predicted time point of reach of said cumulative dose to a stop threshold according to said start time and said acquisition time;
stopping said irradiation of said x-ray radiation from said x-ray radiation generating apparatus at said predicted time point.

17. An x-ray imaging system including an x-ray radiation generating apparatus for emitting x-ray radiation and an x-ray imaging apparatus for detecting an x-ray radiation image of an object, comprising:
a detection panel, having plural pixels, for detecting a dose of x-ray radiation received by said object exposed to said x-ray radiation from said x-ray radiation generating apparatus; said detection panel for storing signal charge according to the detected x-ray radiation and outputting an image signal from the detected x-ray radiation, for generating an image of said object;
an x-ray radiation monitoring device for monitoring said x-ray radiation incident upon said detection panel;
a dose sampler for sampling a dose signal of said dose of said x-ray radiation per unit time according to an output of said x-ray radiation monitoring device;
a start detector for detecting a start of irradiation of said x-ray radiation from said x-ray radiation generating apparatus according to comparison of said dose signal with a predetermined start threshold;
an autoexposure control device for acquiring cumulative dose of said x-ray radiation according to said dose signal from a start time of the start of irradiation detected by said start detector until acquisition time at which the dose sampler samples the dose signal, for estimating a predicted time point of reach of said cumulative dose to a stop threshold according to said start time and said acquisition time, and for stopping said irradiation of said x-ray radiation from said x-ray radiation generating apparatus at said predicted time point.

* * * * *